United States Patent
Godo

(10) Patent No.: US 10,575,717 B2
(45) Date of Patent: Mar. 3, 2020

(54) CAPSULE ENDOSCOPE, CAPSULE ENDOSCOPE SYSTEM, AND METHOD FOR CONTROLLING CAPSULE ENDOSCOPE

(71) Applicant: OLYMPUS CORPORATION, Tokyo (JP)

(72) Inventor: Hirokazu Godo, Tokyo (JP)

(73) Assignee: OLYMPUS CORPORATION, Tokyo (JP)

(*) Notice: Subject to any disclaimer, the term of this patent is extended or adjusted under 35 U.S.C. 154(b) by 324 days.

(21) Appl. No.: 15/413,648

(22) Filed: Jan. 24, 2017

(65) Prior Publication Data

US 2017/0127922 A1 May 11, 2017

Related U.S. Application Data

(63) Continuation of application No. PCT/JP2014/071014, filed on Aug. 8, 2014.

(51) Int. Cl.
A61B 1/04 (2006.01)
A61B 1/00 (2006.01)
A61B 5/07 (2006.01)

(52) U.S. Cl.
CPC .......... *A61B 1/041* (2013.01); *A61B 1/00006* (2013.01); *A61B 1/00009* (2013.01);
(Continued)

(58) Field of Classification Search
CPC . A61B 1/041; A61B 1/00006; A61B 1/00009; A61B 1/00016; A61B 1/00045; A61B 1/00158; A61B 5/073
See application file for complete search history.

(56) References Cited

U.S. PATENT DOCUMENTS

2006/0155174 A1* 7/2006 Glukhovsky ...... A61B 1/00036
600/301
2007/0191671 A1 8/2007 Kawano et al.
(Continued)

FOREIGN PATENT DOCUMENTS

JP 2006-223892 A 8/2006
JP 2008-237639 A 10/2008
(Continued)

OTHER PUBLICATIONS

International Search Report dated Nov. 11, 2014 issued in PCT/JP2014/071014.

*Primary Examiner* — Timothy J Neal
*Assistant Examiner* — William B Chou
(74) *Attorney, Agent, or Firm* — Scully, Scott, Murphy & Presser, P.C.

(57) ABSTRACT

A capsule endoscope includes: an imaging unit that images a subject and to acquire an image of the subject and is set to either of a first mode and a second mode; a data acquiring unit that acquires data other than an image; and a control unit that switches a mode of the imaging unit between the first mode and the second mode based on an analysis result of the image and an analysis result of the data. The control unit switches the mode of the imaging unit to the second mode based on the analysis result of the data when the mode of the imaging unit is set to the first mode, and switches the mode of the imaging unit to the first mode based on the analysis result of the image when the mode of the imaging unit is set to the second mode.

17 Claims, 14 Drawing Sheets

(52) U.S. Cl.
CPC ...... *A61B 1/00016* (2013.01); *A61B 1/00045* (2013.01); *A61B 1/00158* (2013.01); *A61B 5/073* (2013.01)

(56) References Cited

U.S. PATENT DOCUMENTS

| | | | |
|---|---|---|---|
| 2008/0242926 A1 | 10/2008 | Nishino | |
| 2008/0242931 A1 | 10/2008 | Nishino | |
| 2010/0210903 A1* | 8/2010 | Ishihara | A61B 1/00004 600/109 |

FOREIGN PATENT DOCUMENTS

| | | |
|---|---|---|
| JP | 2008-237640 A | 10/2008 |
| JP | 2009-178180 A | 8/2009 |
| JP | 2009-195271 A | 9/2009 |
| JP | 2013-511320 A | 4/2013 |
| WO | WO 2007/083708 A1 | 7/2007 |
| WO | WO 2011/061746 A1 | 5/2011 |

* cited by examiner

CAPSULE ENDOSCOPE, CAPSULE ENDOSCOPE SYSTEM, AND METHOD FOR CONTROLLING CAPSULE ENDOSCOPE

This application is a continuation application based on a PCT International Application No. PCT/JP2014/071014 filed on Aug. 8, 2014, the content of which is incorporated herein by reference.

BACKGROUND OF THE INVENTION

Field of the Invention

The present invention relates to a capsule endoscope, a capsule endoscope system, and a method of controlling a capsule endoscope.

Description of Related Art

When a capsule endoscope is passing through an organ of a subject, that is, when a capsule endoscope is moving relative to a human body, and a moving speed is high, it is preferable that an imaging frame rate be increased to reduce missed imaging of a subject. When the capsule endoscope stops relative to the human body, it is preferable that the imaging frame rate be decreased to reduce power consumption of the capsule endoscope.

Japanese Unexamined Patent Application, First Publication No. 2006-223892 discloses a method of controlling a frame rate of a capsule endoscope. In this method, the frame rate is controlled on the basis of a process of comparing images of a plurality of frames. Alternatively, in this method, the frame rate is controlled on the basis of data measured by a sensor such as an acceleration sensor.

SUMMARY OF THE INVENTION

According to a first aspect of the present invention, a capsule endoscope includes: an imaging unit configured to image a subject and to acquire an image of the subject, the imaging unit being set to either of a first mode and a second mode; a data acquiring unit configured to acquire data other than an image; and a control unit configured to switch a mode of the imaging unit between the first mode and the second mode on the basis of an analysis result of the image and an analysis result of the data, wherein the control unit switches the mode of the imaging unit to the second mode on the basis of the analysis result of the data when the mode of the imaging unit is set to the first mode, and switches the mode of the imaging unit to the first mode on the basis of the analysis result of the image when the mode of the imaging unit is set to the second mode.

According to a second aspect of the present invention, in the capsule endoscope according to the first aspect, a cycle with which the analysis result of the data is acquired by the control unit may be shorter than a cycle with which the analysis result of the image is acquired by the control unit.

According to a third aspect of the present invention, in the capsule endoscope according to the first aspect, the data acquiring unit may acquire at least one of acceleration data, velocity data, angular velocity data, position data, and magnetism data.

According to a fourth aspect of the present invention, in the capsule endoscope according to the first aspect, an imaging frame rate in the first mode may be lower than an imaging frame rate in the second mode.

According to a fifth aspect of the present invention, the capsule endoscope according to the first aspect may further include an image analyzing unit configured to analyze the image acquired by the imaging unit.

According to a sixth aspect of the present invention, the capsule endoscope according to the first aspect may further include a data analyzing unit configured to analyze the data acquired by the data acquiring unit.

According to a seventh aspect of the present invention, in the capsule endoscope according to the fourth aspect, the mode of the imaging unit may be set to any one of the first mode, the second mode, and a third mode, an imaging frame rate in the third mode may be higher than the imaging frame rate in the second mode, and the control unit may switch the mode of the imaging unit to the first mode or the third mode on the basis of the analysis result of the image when the mode of the imaging unit is set to the second mode.

According to an eighth aspect of the present invention, in the capsule endoscope according to the fourth aspect, the mode of the imaging unit may be set to any one of the first mode, the second mode, and a fourth mode, the imaging frame rate in the fourth mode may be lower than the imaging frame rate in the first mode, and the control unit may switch the mode of the imaging unit to the first mode on the basis of the analysis result of the data when the mode of the imaging unit is set to the fourth mode.

According to a ninth aspect of the present invention, in the capsule endoscope according to the first aspect, a cycle with which the analysis result of the image is acquired by the control unit when the mode of the imaging unit is set to the second mode may be shorter than a cycle with which the analysis result of the image is acquired by the control unit when the mode of the imaging unit is set to the first mode.

According to a tenth aspect of the present invention, the capsule endoscope according to the first aspect may further include a wireless communication unit configured to receive motion information used for identifying a first case in which the motion of a human body is relatively small and a second case in which the motion of the human body is relatively large, and the control unit may switch the mode of the imaging unit to the second mode on the basis of the analysis result of the data only when the mode of the imaging unit is set to the first mode and the motion of the human body is relatively small.

According to a eleventh aspect of the present invention, in the capsule endoscope according to the first aspect, the control unit may switch the mode of the imaging unit to the second mode on the basis of the analysis result of the data regardless of the analysis result of the image when the mode of the imaging unit is set to the first mode, and the control unit may switch the mode of the imaging unit to the first mode on the basis of the analysis result of the image regardless of the analysis result of the data when the second mode is set in the imaging unit.

According to a twelfth aspect of the present invention, in the capsule endoscope according to the first aspect, the control unit may switch the mode of the imaging unit to the second mode on the basis of a motion of the capsule endoscope which is the analysis result of the data when the imaging unit is set to the first mode, and the control unit may switch the mode of the imaging unit to the first mode on the basis of the motion of the capsule endoscope which is the analysis result of the image when the imaging unit is set to the second mode.

According to a thirteenth aspect of the present invention, in the capsule endoscope according to the twelfth aspect, the control unit may switch the mode of the imaging unit to the second mode on the basis of the motion of the capsule endoscope which is calculated from a variation of the data at a plurality of times when the imaging unit is set to the first mode, and the control unit may switch the mode of the imaging unit to the first mode on the basis of the motion of the capsule endoscope which is calculated from a variation of the image at a plurality of times when the imaging unit is set to the second mode.

According to a fourteenth aspect of the present invention, in the capsule endoscope according to the eleventh aspect, the control unit may switch the mode of the imaging unit to the second mode on the basis of a motion of the capsule endoscope which is the analysis result of the data when the imaging unit is set to the first mode, and the control unit may switch the mode of the imaging unit to the first mode on the basis of the motion of the capsule endoscope which is the analysis result of the image when the imaging unit is set to the second mode.

According to a fifteenth aspect of the present invention, in the capsule endoscope according to the fourteenth aspect, the control unit may switch the mode of the imaging unit to the second mode on the basis of the motion of the capsule endoscope which is calculated from a variation of the data at a plurality of times when the imaging unit is set to the first mode, and the control unit may switch the mode of the imaging unit to the first mode on the basis of the motion of the capsule endoscope which is calculated from a variation of the image at a plurality of times when the imaging unit is set to the second mode.

According to an sixteenth aspect of the present invention, a capsule endoscope system includes a capsule endoscope and a receiver device, wherein the capsule endoscope includes: an imaging unit configured to image a subject and to acquire an image of the subject in a state in which any one of a first mode and a second mode is set; a data acquiring unit configured to acquire data other than an image; a control unit configured to switch a mode of the imaging unit between the first mode and the second mode on the basis of an analysis result of the image and an analysis result of the data; and a first wireless communication unit configured to transmit the image acquired by the imaging unit to the receiver device, the control unit switches the mode of the imaging unit to the second mode on the basis of the analysis result of the data when the mode of the imaging unit is set to the first mode, and switches the mode of the imaging unit to the first mode on the basis of the analysis result of the image when the mode of the imaging unit of the second mode, and the receiver device includes a second wireless communication unit configured to receive the image transmitted from the capsule endoscope.

According to a seventeenth aspect of the present invention, a method of controlling a capsule endoscope includes: a first step of acquiring an image of a subject using an imaging unit configured to image the subject and to acquire the image of the subject when the imaging unit is set to either of a first mode and a second mode; a second step of acquiring data other than an image; and a third step of switching a mode of the imaging unit between the first mode and the second mode on the basis of an analysis result of the image and an analysis result of the data, wherein the third step includes switching the mode of the imaging unit to the second mode on the basis of the analysis result of the data when the mode of the imaging unit is set to the first mode and switching the mode of the imaging unit to the first mode on the basis of the analysis result of the image when the mode of the imaging unit is set to the second mode.

DETAILED DESCRIPTION OF THE INVENTION

Hereinafter, embodiments of the present invention will be described with reference to the accompanying drawings.
(First Embodiment)

Figure 1:
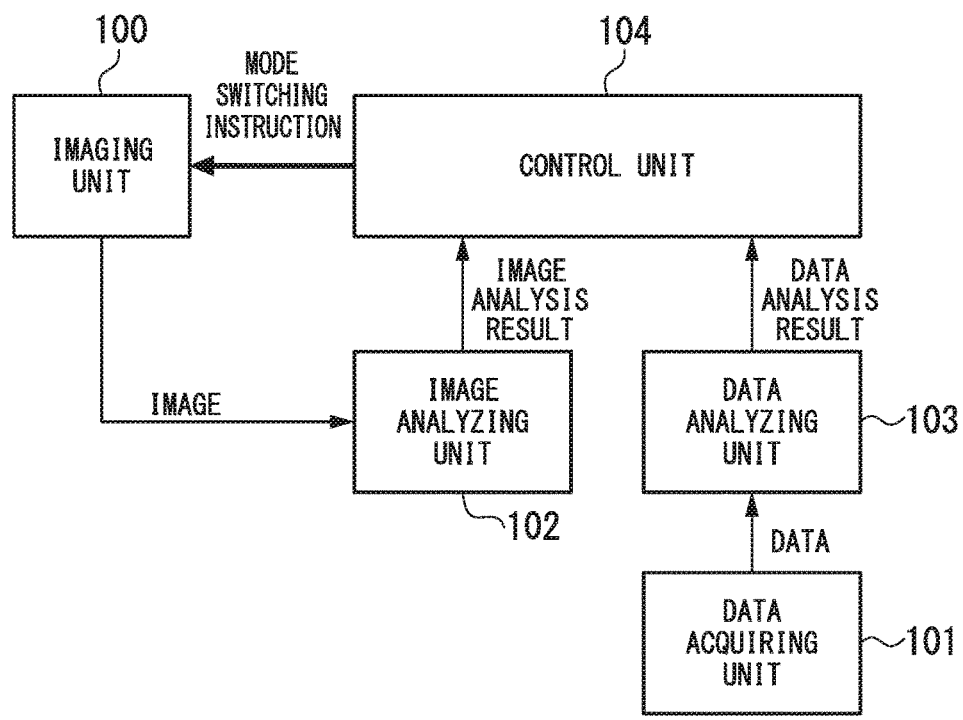
FIG. 1 is a block diagram showing a configuration of a capsule endoscope according to a first embodiment of the present invention.

FIG. 1 shows a configuration of a capsule endoscope 10 according to a first embodiment of the present invention. As shown in FIG. 1, the capsule endoscope 10 includes an imaging unit 100, a data acquiring unit 101, an image analyzing unit 102, a data analyzing unit 103, and a control unit 104.

The mode of the imaging unit 100 is set to any one of a first mode and a second mode. The imaging unit 100 images a subject and acquires an image (image data) of the subject. For example, the subject is an organ in a human body. The image acquired by the imaging unit 100 is output to the image analyzing unit 102.

The data acquiring unit 101 acquires data other than an image. For example, the data acquiring unit 101 acquires at least one of acceleration data, velocity data, angular velocity data, position (distance) data, and magnetism data. The data acquired by the data acquiring unit 101 is output to the data analyzing unit 103.

The image analyzing unit 102 analyzes the image acquired by the imaging unit 100. The analysis result of the image is output to the control unit 104. The data analyzing unit 103 analyzes the data acquired by the data acquiring unit 101. The analysis result of the data is output to the control unit 104.

The control unit 104 switches a mode of the imaging unit 100 between a first mode and a second mode on the basis of the analysis result of the image and the analysis result of the data. The control unit 104 switches the mode of the imaging unit 100 to the second mode on the basis of the analysis result of the data when the mode of the imaging unit 100 is set to the first mode. The control unit 104 switches the mode of the imaging unit 100 to the first mode on the basis of the analysis result of the image when the imaging unit 100 is set to the second mode. When the mode of the imaging unit 100 is switched, the control unit 104 outputs a mode switching instruction to the imaging unit 100. The imaging unit 100 changes imaging parameters therein to values based on the mode in response to the mode switching instruction.

A computer in the capsule endoscope 10 may read a program defining operations of the image analyzing unit 102, the data analyzing unit 103, and the control unit 104 and execute the read program. That is, the functions of the image analyzing unit 102, the data analyzing unit 103, and the control unit 104 may be realized as software functions. The program may be provided by a "computer-readable recording medium" such as a flash memory. The program may be transmitted from a computer having a storage device having the program stored therein or the like to the capsule endoscope 10 via a transmission medium or by carrier waves in the transmission medium. The "transmission medium" for transmitting the program is a medium having a function of transmitting information like a network (a communication network) such as the internet or a communication circuit (a communication line) such as a telephone line. The program may realize a part of the above-mentioned functions. The program may be a so-called differential file (a differential program) which can realize the above-mentioned functions in combination with a program which has been recorded in advance in the computer.

Figure 2:
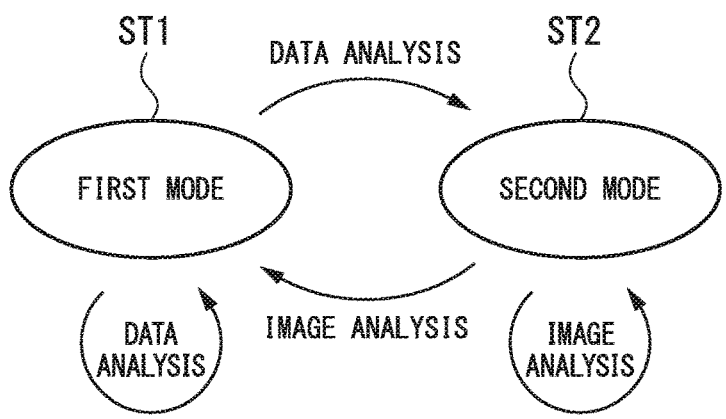
FIG. 2 is a reference diagram showing a state transition of an imaging unit in the first embodiment of the present invention.

FIG. 2 shows a state transition of the imaging unit 100. In a state ST1 in which the mode of the imaging unit 100 is set to the first mode, the control unit 104 determines the mode on the basis of the analysis result of data. For example, the analysis result of data is a result of comparison of data (data on acceleration, velocity, or angular velocity) with a predetermined threshold value. Alternatively, the analysis result of data is a result of comparison of a variation of data (data on position or magnetism) at a plurality of times with a predetermined threshold value.

When data or a variation thereof is equal to or greater than a predetermined threshold value, the control unit 104 determines that the mode of the imaging unit 100 is to be switched. When data or a variation thereof is less than a predetermined threshold value, the control unit 104 determines that the mode of the imaging unit 100 is not to be switched. When the control unit 104 determines that the mode of the imaging unit 100 is to be switched, the control unit 104 switches the mode of the imaging unit 100 to the second mode. As a result, the imaging unit 100 is in a state ST2 in which the second mode is set.

In the state ST2, the control unit 104 determines the mode on the basis of the analysis result of an image. For example, the analysis result of an image is a result of comparison of a variation of an image at a plurality of times with a predetermined threshold value. For example, the variation of an image is a variation of a value of all or some pixels constituting the image. The threshold value associated with the analysis of an image and the threshold value associated with the analysis of data do not have to be equal to each other.

When the variation of an image is equal to or greater than the predetermined value, the control unit 104 determines that the mode of the imaging unit 100 is not to be switched. When the variation of an image is less than the predetermined value, the control unit 104 determines that the mode of the imaging unit 100 is to be switched. When the control unit 104 determines that the mode of the imaging unit 100 is to be switched, the control unit 104 switches the mode of the imaging unit 100 to the first mode. As a result, the imaging unit 100 is in a state ST1 in which the first mode is set. As described above, the mode of the imaging unit 100 is switched between the first mode and the second mode. In this example, it is determined that the mode is to be switched from the second mode to the first mode when the variation of an image is less than the threshold value. However, in either of the case in which the variation of an image is less than the threshold value or the case in which the variation of an image is equal to or greater than the threshold value, whether to switch the mode can be appropriately controlled by an algorithm or the like.

For example, when the capsule endoscope 10 stops or when the motion of the capsule endoscope 10 is slow, the mode of the imaging unit 100 is set to the first mode. When the motion of the capsule endoscope 10 is fast, the mode of the imaging unit 100 is set to the second mode.

Figure 3:
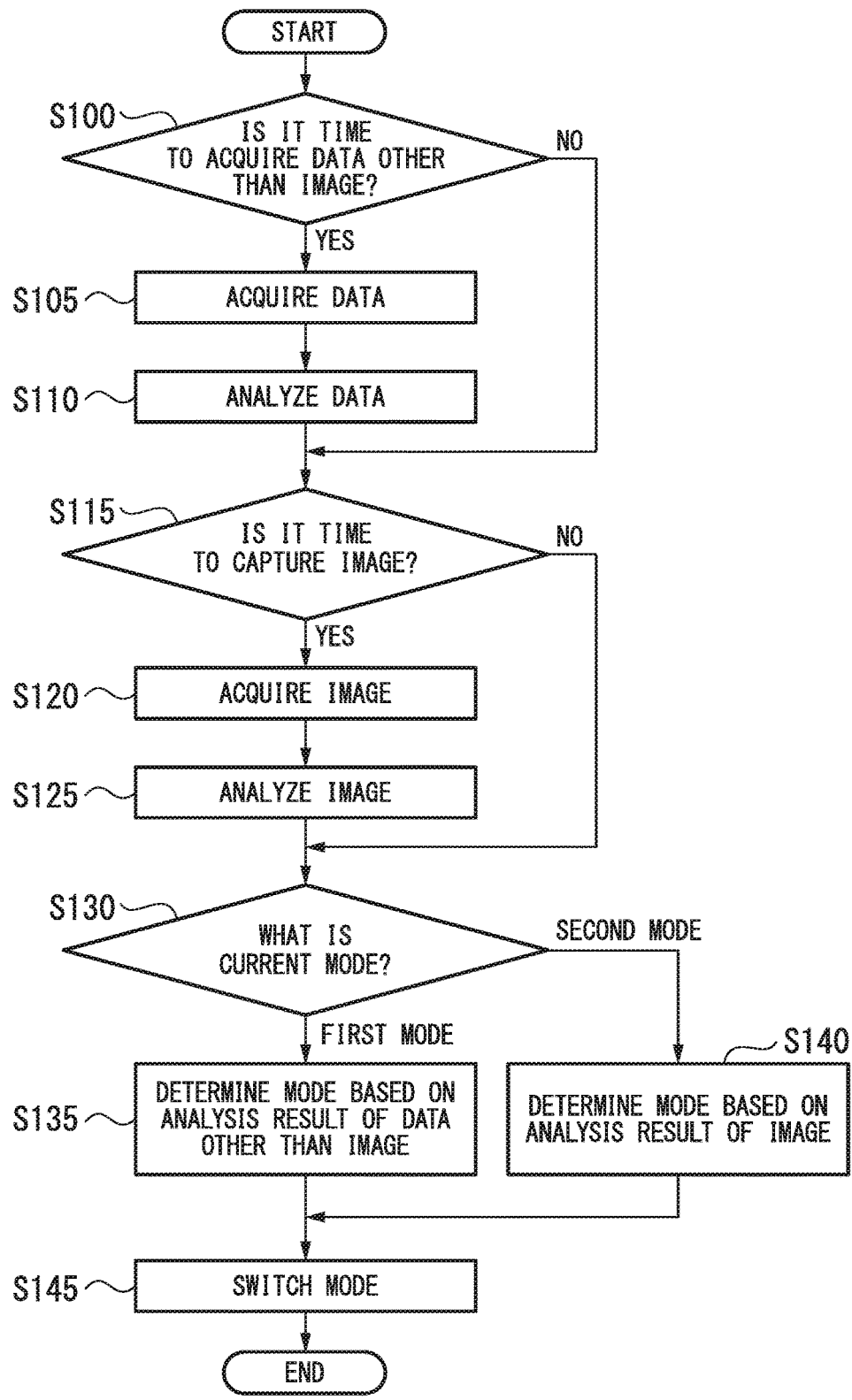
FIG. 3 is a flowchart showing a method of controlling the capsule endoscope according to the first embodiment of the present invention.

FIG. 3 shows a method of controlling the capsule endoscope 10. When it is time to acquire data other than an image after a process is started (YES in Step S100), the data acquiring unit 101 acquires data (Step S105). For example, the data acquiring unit 101 acquires data with a predetermined cycle. When a time corresponding to the cycle elapses after data is acquired, the data acquiring unit 101 acquires data again. The acquired data is output to the data analyzing unit 103 from the data acquiring unit 101.

After the data is acquired, the data analyzing unit 103 analyzes the acquired data (Step S110). The analysis result of data is output to the control unit 104 from the data analyzing unit 103. When it is not time to acquire data other than an image (NO in Step S100), the processes of Steps S105 and S110 are not performed.

When it is time to capture an image after the data is analyzed (YES in Step S115), the imaging unit 100 performs imaging and acquires an image of a subject (Step S120). For example, the imaging unit 100 performs imaging with a predetermined cycle. When a time corresponding to the cycle elapses after the imaging is performed, the imaging unit 100 performs imaging again. The acquired image is output to the image analyzing unit 102 from the imaging unit 100.

After the image is acquired, the image analyzing unit 102 analyzes the acquired image (Step S125). The analysis result of an image is output to the control unit 104. When it is not time to capture an image (NO in Step S115), the processes of Steps S120 and S125 are not performed.

After the image is analyzed, the process flow branches depending on the mode set in the imaging unit 100 (Step S130). When the mode of the imaging unit 100 is the first mode, the control unit 104 determines the mode which is to be set in the imaging unit 100 on the basis of the analysis result of data (Step S135). On the other hand, when the mode of the imaging unit 100 is the second mode, the control unit 104 determines the mode which is to be set in the imaging unit 100 on the basis of the analysis result of an image (Step S140).

After the mode is determined, the control unit 104 switches the mode of the imaging unit 100 to the mode determined in Step S135 or S140 (Step S145). When the mode determined in Step S135 or S140 is the same as the mode of the imaging unit 100, the mode is not switched. That is, the process of Step S145 is not performed.

After the mode is switched, the mode switching process ends. The process flow shown in FIG. 3 is repeatedly performed.

In FIG. 3, the processes of Steps S115, S120, and S125 are performed after the processes of Steps S100, S105, and S110. However, the processes of Steps S100, S105, and S110 may be performed after the processes of Steps S115, S120, and S125.

A cycle with which the control unit 104 acquires the analysis result of data may be shorter than a cycle with which the control unit 104 acquires the analysis result of an image. That is, a cycle with which the analysis result of data is output to the control unit 104 from the data analyzing unit 103 may be shorter than a cycle with which the analysis result of an image is output to the control unit 104 from the image analyzing unit 102. Accordingly, when the mode of the imaging unit 100 is set to the first mode, it is possible to more rapidly switch the mode from the first mode to the second mode. A cycle with which the data analyzing unit 103 performs the data analysis may be shorter than a cycle with which the image analyzing unit 102 performs the image analysis.

The cycle with which the control unit 104 acquires the analysis result of an image when the mode of the imaging unit 100 is set to the second mode may be shorter than the cycle with which the control unit 104 acquires the analysis result of an image when the mode of the imaging unit 100 is set to the first mode. That is, the cycle with which the analysis result of an image is output to the control unit 104 from the image analyzing unit 102 when the mode of the imaging unit 100 is set to the second mode may be shorter than the cycle with which the analysis result of an image is output to the control unit 104 from the image analyzing unit 102 when the mode of the imaging unit 100 is set to the first mode. Accordingly, when the mode of the imaging unit 100 is set to the second mode, it is possible to more rapidly switch the mode from the second mode to the first mode.

(Modified Example)

Figure 4:
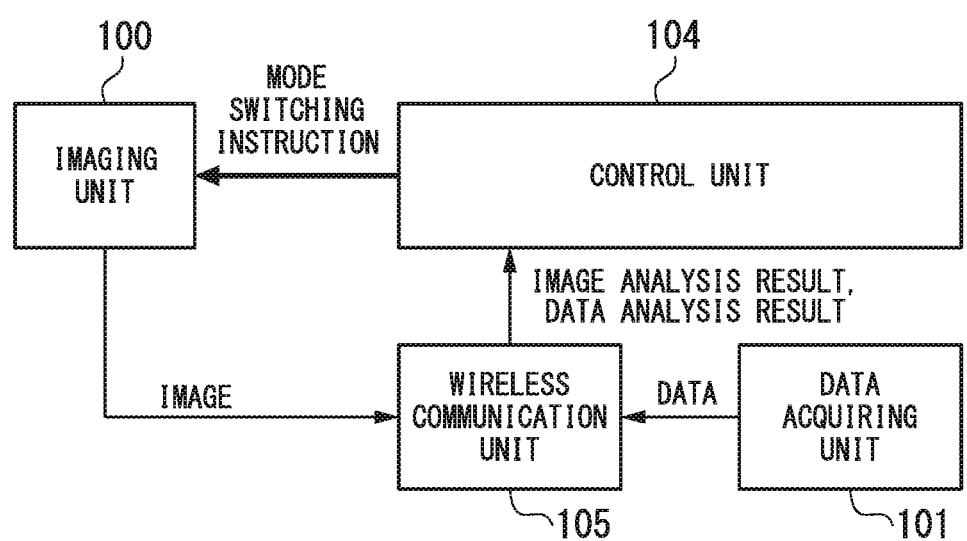
FIG. 4 is a block diagram showing a configuration of a capsule endoscope according to a modified example of the first embodiment of the present invention.

FIG. 4 shows a configuration of a capsule endoscope 11 according to a modified example of the first embodiment. As shown in FIG. 4, the capsule endoscope 101 includes an imaging unit 100, a data acquiring unit 101, a control unit 104, and a wireless communication unit 105 (a first wireless communication unit).

The imaging unit 100 is the same as the imaging unit 100 in the capsule endoscope 10 shown in FIG. 1. The data acquiring unit 101 is the same as the data acquiring unit 101 in the capsule endoscope 10 shown in FIG. 1. The control unit 104 is the same as the control unit 104 in the capsule endoscope 10 shown in FIG. 1.

The image acquired by the imaging unit 100 is output to the wireless communication unit 105. The data acquired by the data acquiring unit 101 is output to the wireless communication unit 105. The wireless communication unit 105 wirelessly transmits the image acquired by the imaging unit 100 to a receiver device. The wireless communication unit 105 wirelessly transmits the data acquired by the data acquiring unit 101 to the receiver device. The wireless communication unit 105 wirelessly receives the analysis result of the image and the analysis result of the data from the receiver device. The analysis result of the image and the analysis result of the data received by the wireless communication unit 105 is output to the control unit 104.

The receiver device receives the image and the data transmitted from the wireless communication unit 105. The receiver device analyzes the received image. The receiver device analyzes the received data. The receiver device wirelessly transmits the analysis result of the image to the capsule endoscope 11. The receiver device wirelessly transmits the analysis result of the data to the capsule endoscope 11.

As shown in FIG. 4, the capsule endoscope 11 does not include the image analyzing unit 102 and the data analyzing unit 103. Accordingly, the image analyzing unit 102 and the data analyzing unit 103 are not essential for the first embodiment. The capsule endoscope 11 may include one of the image analyzing unit 102 and the data analyzing unit 103 and the receiver device may include the other of the image analyzing unit 102 and the data analyzing unit 103.

Figure 5:
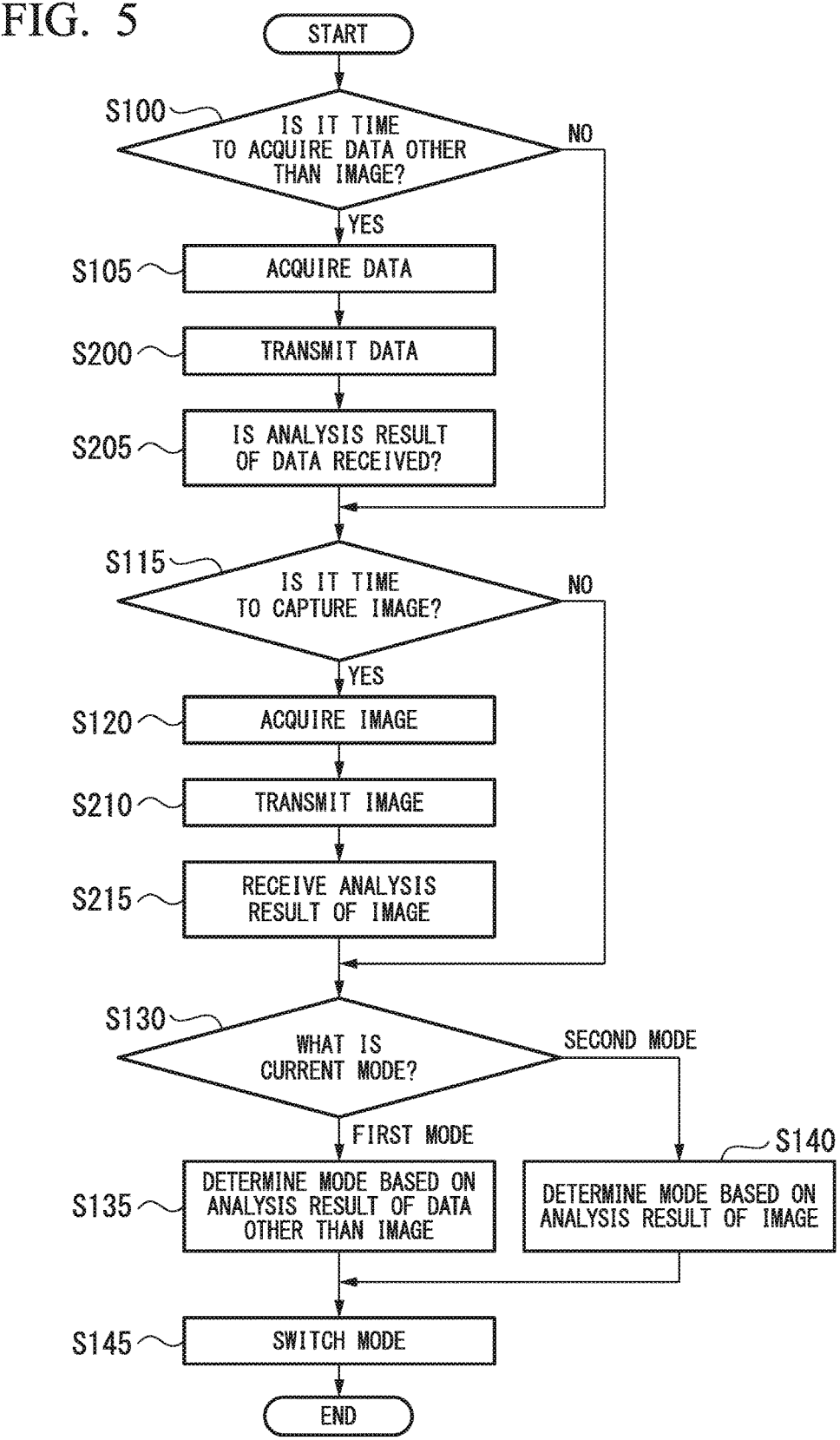
FIG. 5 is a flowchart showing a method of controlling the capsule endoscope according to the modified example of the first embodiment of the present invention.

FIG. 5 shows a method of controlling the capsule endoscope 11. A difference of the process flow shown in FIG. 5 from the process flow shown in FIG. 3 will be described below.

After data is acquired in Step S105, the wireless communication unit 105 wirelessly transmits the acquired data to the receiver device (Step S200). After the data is transmitted, the wireless communication unit 105 wirelessly receives the analysis result of the data transmitted from the receiver device (Step S205). When it is not time to acquire data other than an image (NO in Step S100), the processes of Steps S105, S200, and S205 are not performed. After the analysis result of the data is received, the determination of Step S115 is performed.

After an image is acquired in Step S120, the wireless communication unit 105 wirelessly transmits the acquired image to the receiver device (Step S210). After the image is transmitted, the wireless communication unit 105 wirelessly receives the analysis result of the image transmitted from the receiver device (Step S215). When it is not time to capture an image (NO in Step S115), the processes of Steps S120, S210, and S215 are not performed. After the analysis result of the data is received, the process flow branches depending on the mode set in the imaging unit 100 (Step S130).

Except for the above-mentioned points, the process flow shown in FIG. 5 is the same as the process flow shown in FIG. 3.

In FIG. 5, the processes of Steps S115, S120, S210, and S215 are performed after the processes of Steps S100, S105, S200, and S205. However, the processes of Steps S100, S105, S200, and S205 may be performed after the processes of S115, Steps S120, S210, and S215.

In the capsule endoscope 10 shown in FIG. 1, communication of an image and communication of an analysis result of the image are not necessary in comparison with the capsule endoscope 11 shown in FIG. 4. In the capsule endoscope 10 shown in FIG. 1, communication of data other than an image and communication of an analysis result of the data are not necessary in comparison with the capsule endoscope 11 shown in FIG. 4. Accordingly, in the capsule endoscope 10 shown in FIG. 1, it is possible to reduce the delay required for switching the mode.

According to the first embodiment, the capsule endoscope 10 or 11 includes the imaging unit 100 configured to image a subject and to acquire an image of the subject, any one of the first mode and the second mode being set in the imaging unit, the data acquiring unit 101 configured to acquire data other than an image, and the control unit 104 configured to switch the mode of the imaging unit 100 between the first mode and the second mode on the basis of the analysis result of the image and the analysis result of the data, and the control unit 104 switches the mode of the imaging unit 100 to the second mode on the basis of the analysis result of the data when the mode of the imaging unit 100 is set to the first mode, and switches the mode of the imaging unit 100 to the first mode on the basis of the analysis result of the image when the mode of the imaging unit 100 is set to the second mode.

According to the first embodiment, the method of controlling the capsule endoscope 10 or 11 includes a first step S120 of acquiring an image using the imaging unit 100 configured to image a subject and to acquire an image of the subject in a state in which any one of the first mode and the second mode is set, a second step S100 of acquiring data other than an image, and a third step S145 of switching a mode of the imaging unit 100 between the first mode and the second mode on the basis of an analysis result of the image and an analysis result of the data, and the third step S145 includes switching the mode of the imaging unit 100 to the second mode on the basis of the analysis result of the data when mode of the imaging unit 100 is set to the first mode and switching the mode of the imaging unit 100 to the first mode on the basis of the analysis result of the image when the mode of the imaging unit 100 is set to the second mode.

In the first embodiment, when the mode of the imaging unit 100 is set to the first mode, the mode of the imaging unit 100 is switched to the second mode on the basis of the analysis result of the data. When the imaging unit 100 is set to the second mode, the mode of the imaging unit 100 is switched to the first mode on the basis of the analysis result of the image. Accordingly, it is possible to control the imaging mode more accurately.

For example, a data analysis result acquisition frequency in the first mode may be higher than that in the second mode. Accordingly, it is possible to more rapidly switch the mode from the first mode to the second mode. The mode determination based on the analysis result of the image can be more accurate than the mode determination based on the analysis result of the data. Accordingly, it is possible to more accurately switch the mode from the second mode to the first mode. As a result, it is possible to control the imaging mode more accurately.

An imaging frame rate in the second mode may be higher than that in the first mode. For example, when the capsule endoscope 10 or the capsule endoscope 11 stops or when the capsule endoscope 10 or the capsule endoscope 11 moves slowly, the mode of the imaging unit 100 is set to the first mode. When the capsule endoscope 10 or the capsule endoscope 11 moves fast, an image is likely to blur. Accordingly, the mode of the imaging unit 100 is set to the second mode such that an image becomes clearer when the frame rate is increased.

A compression ratio in an image compressing process in the second mode may be lower than that in the first mode. For example, when the capsule endoscope 10 or the capsule endoscope 11 stops or when the capsule endoscope 10 or the capsule endoscope 11 moves slowly, the mode of the imaging unit 10 is set to the first mode. When the capsule endoscope 10 or the capsule endoscope 11 moves fast, an image is likely to blur. Accordingly, the mode of the imaging unit 100 is set to the second mode such that an image becomes clearer by decreasing the compression ratio.

A resolution of an image in the second mode may be lower than that in the first mode. For example, when the capsule endoscope 10 or the capsule endoscope 11 stops or when the capsule endoscope 10 or the capsule endoscope 11 moves slowly, the mode of the imaging unit 100 is set to the first mode. When the capsule endoscope 10 or the capsule endoscope 11 moves fast, an image is likely to blur. Accordingly, the mode of the imaging unit 100 is set to the second mode such that an image becomes clearer pixels of the image thin out.

An exposure period in the second mode may be shorter than that in the first mode. For example, when the capsule endoscope 10 or the capsule endoscope 11 stops or when the capsule endoscope 10 or the capsule endoscope 11 moves slowly, the mode of the imaging unit 100 is set to the first mode. When the capsule endoscope 10 or the capsule endoscope 11 moves fast, an image is likely to blur. Accordingly, the mode of the imaging unit 100 is set to the second mode such that an image becomes clearer as the exposure period is shortened.

An angle of view in the second mode may be lower than that in the first mode. For example, when the capsule endoscope 10 or the capsule endoscope 11 stops or when the capsule endoscope 10 or the capsule endoscope 11 moves slowly, the mode of the imaging unit is set to the first mode. When the capsule endoscope 10 or the capsule endoscope 11 moves fast, an image is likely to blur. Accordingly, the mode of the imaging unit 100 is set to the second mode such that an image becomes clearer the angle of view is decreased.

(Second Embodiment)

Figure 6:
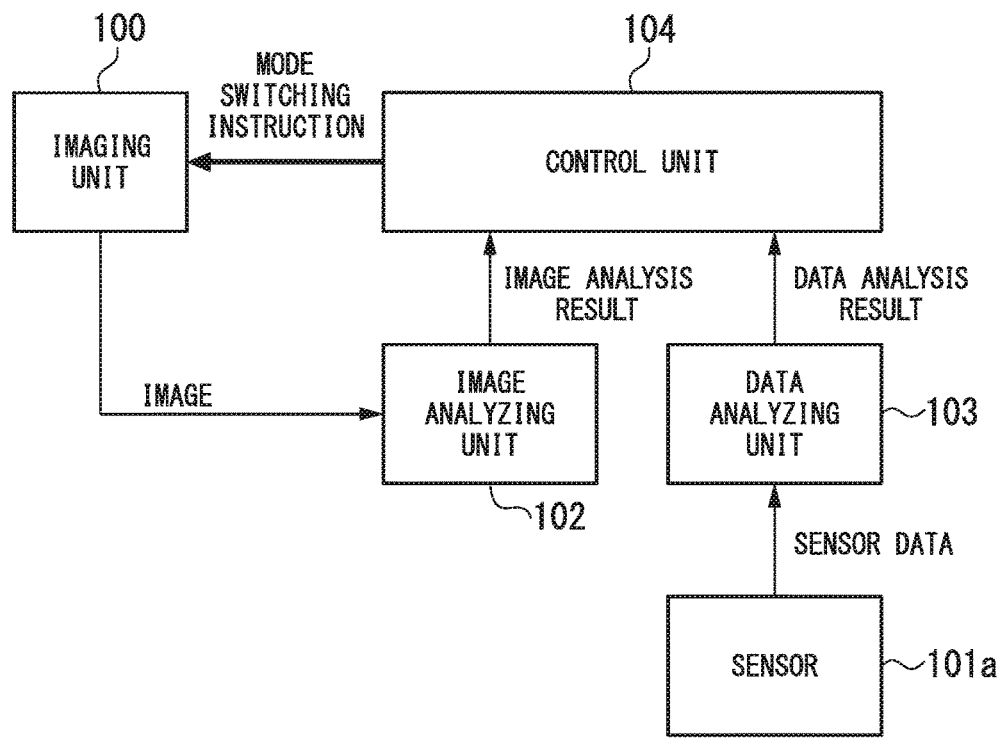
FIG. 6 is a block diagram showing a configuration of a capsule endoscope according to a second embodiment of the present invention.

FIG. 6 shows a configuration of a capsule endoscope 12 according to a second embodiment of the present invention. As shown in FIG. 6, the capsule endoscope 12 includes an imaging unit 100, a sensor 101a, an image analyzing unit 102, a data analyzing unit 103, and a control unit 104.

The imaging unit 100 is the same as the imaging unit 100 in the capsule endoscope 10 shown in FIG. 1. The image analyzing unit 102 is the same as the image analyzing unit 102 in the capsule endoscope 10 shown in FIG. 1. The data analyzing unit 103 is the same as the data analyzing unit 103 in the capsule endoscope 10 shown in FIG. 1. The control unit 104 is the same as the control unit 104 in the capsule endoscope 10 shown in FIG. 1.

The sensor 101a is a specific example of the data acquiring unit 101 in the capsule endoscope 10 shown in FIG. 1. For example, the sensor 101a is one or more of an acceleration sensor, a velocity sensor, a magnetic sensor, and an angular velocity sensor. Accordingly, the sensor 101a can acquire at least one of acceleration data, velocity data, angular velocity data, and magnetism data. The sensor 101a outputs sensor data consisting of the acquired data to the data analyzing unit 103.

When the sensor 101a is an acceleration sensor, the sensor data is acceleration data. The acceleration data is an acceleration measurement result of the capsule endoscope 12. It is possible to detect the motion of the capsule endoscope 12 from a variation of the acceleration data at a plurality of times.

When the sensor 101a is a velocity sensor, the sensor data is velocity data. The velocity data is a velocity measurement result of the capsule endoscope 12. It is possible to detect the motion of the capsule endoscope 12 from a variation of the velocity data at a plurality of times.

Position data may be acquired by integrating the velocity indicated by the velocity data. It is possible to detect the motion of the capsule endoscope 12 from a variation of the position data at a plurality of times.

When the sensor 101a is a magnetic sensor, the sensor data is magnetic data. The magnetic data is a geomagnetism measurement result. It is possible to detect a posture of the capsule endoscope 12 using a magnetic sensor capable of measuring magnetism in three-dimensional directions. Accordingly, it is possible to detect the motion of the capsule endoscope 12 from a variation of the magnetic data at a plurality of times.

When the sensor 101a is an angular velocity sensor, the sensor data is angular velocity sensor. The angular velocity data is an angular velocity measurement result of the capsule endoscope 12. It is possible to detect the motion of the capsule endoscope 12 from a variation of the angular velocity data at a plurality of times.

In the second embodiment, the imaging frame rates in the first mode and the second mode are different. The imaging frame rate in the first mode is lower than the imaging frame rate in the second mode. That is, the imaging frame rate in the second mode is higher than the imaging frame rate in the first mode.

Figure 7:
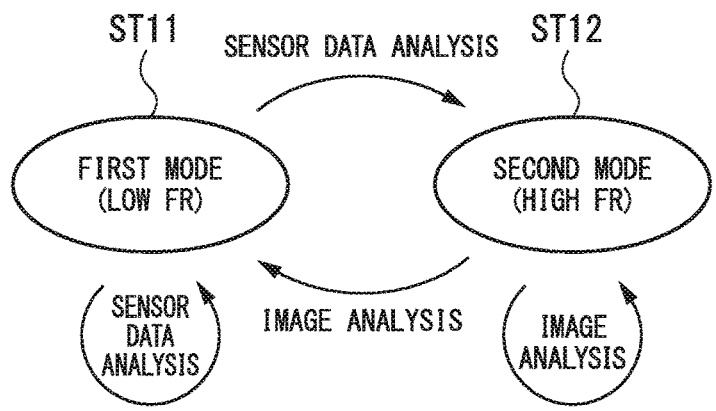
FIG. 7 is a reference diagram showing a state transition of an imaging unit in the second embodiment of the present invention.

FIG. 7 shows a state transition of the imaging unit 100. In a state ST11 in which the mode of the imaging unit 100 is set to the first mode, the control unit 104 determines the mode on the basis of the analysis result of the sensor data. For example, the analysis result of the sensor data is a result of comparison of the sensor data (data on acceleration, velocity, or angular velocity) with a predetermined threshold value. Alternatively, the analysis result of the sensor data is a result of comparison of a variation of the sensor data (data on position or magnetism) at a plurality of times with a predetermined threshold value.

For example, when the sensor data or the variation thereof is equal to or greater than a predetermined threshold value, the control unit 104 determines that the mode of the imaging unit 100 is to be switched. When the sensor data or the variation thereof is less than the predetermined threshold value, the control unit 104 determines that the mode of the imaging unit 100 is not to be switched.

When the control unit 104 determines that the mode of the imaging unit 100 is to be switched, the control unit 104 switches the mode of the imaging unit 100 to the second mode. As a result, the imaging unit 100 is in a state ST12 in which the second mode is set.

In the state ST12, the control unit 104 determines the mode on the basis of the analysis result of the image. For example, when a variation of an image is equal to or greater than a predetermined threshold value, the control unit 104 determines that the mode of the imaging unit 100 is not to be switched. When the variation of the image at a plurality of times is less than the predetermined threshold value, the control unit 104 determines that the mode of the imaging unit 100 is to be switched. When the control unit 104 determines that the mode of the imaging unit 100 is to be switched, the control unit 104 switches the mode of the imaging unit 100 to the first mode. As a result, the imaging unit 100 is in a state ST12 in which the first mode is set. As described above, the mode of the imaging unit 100 is switched between the first mode and the second mode. The threshold value relevant to the analysis of an image and the threshold value relevant to the analysis of the sensor data do not have to be equal to each other.

For example, when the capsule endoscope 12 stops or when the capsule endoscope 12 moves slowly, the mode of the imaging unit 100 is set to the first mode. When the capsule endoscope 12 moves fast, the mode of the imaging unit 100 is set to the second mode.

Figure 8:
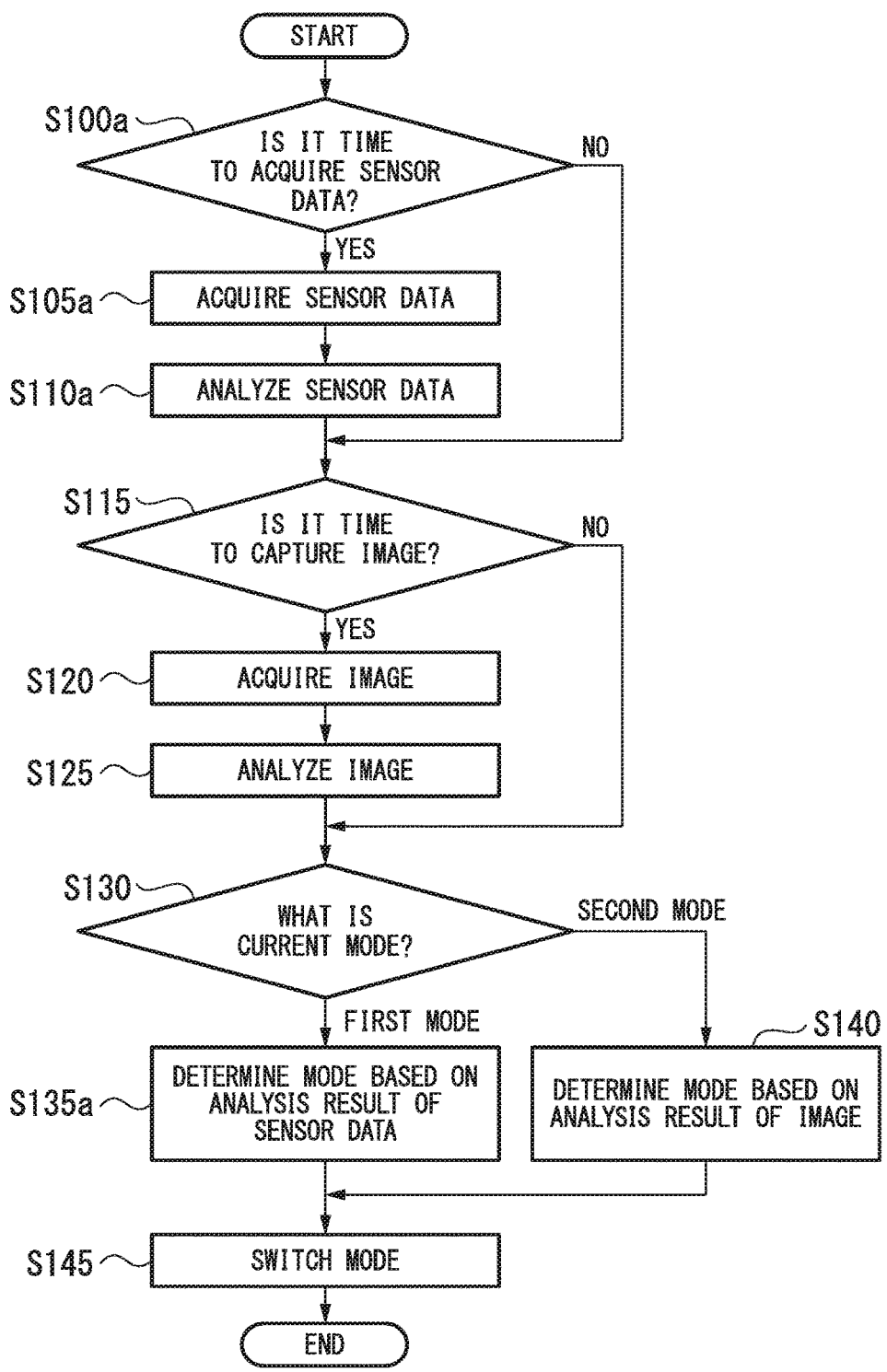
FIG. 8 is a flowchart showing a method of controlling the capsule endoscope according to the second embodiment of the present invention.

FIG. 8 shows a method of controlling the capsule endoscope 12. A difference of the process flow shown in FIG. 8 from the process flow shown in FIG. 3 will be described below.

When it is time to acquire sensor data after the process flow is started (YES in Step S100a), the sensor 101a acquires the sensor data (Step S105a). For example, the sensor 101a acquires the sensor data with a predetermined cycle. When a time corresponding to the cycle elapses after sensor data is acquired, the sensor 101a acquires sensor data again. The acquired sensor data is output to the data analyzing unit 103 from the sensor 101a.

After the sensor data is acquired, the data analyzing unit 103 analyzes the acquired sensor data (Step S110a). The analysis result of the sensor data is output to the control unit 104 from the data analyzing unit 103. When it is not time to acquire the sensor data (NO in Step S100a), the processes of Steps S105a and S110a are not performed.

When the mode of the imaging unit 100 is the first mode after the image is analyzed in Step S125, the control unit 104 determines the mode which is to be set in the imaging unit 100 on the basis of the analysis result of the sensor data (Step S135a).

The processes other than those described above are the same as the processes shown in FIG. 3.

In FIG. 8, the processes of Steps S115, S120, and S125 are performed after processes of Steps S100a, S105a, and S110a. However, the processes of Steps S100a, S105a, and S110a may be performed after the processes of Steps S115, S120, and S125.

Figure 9:
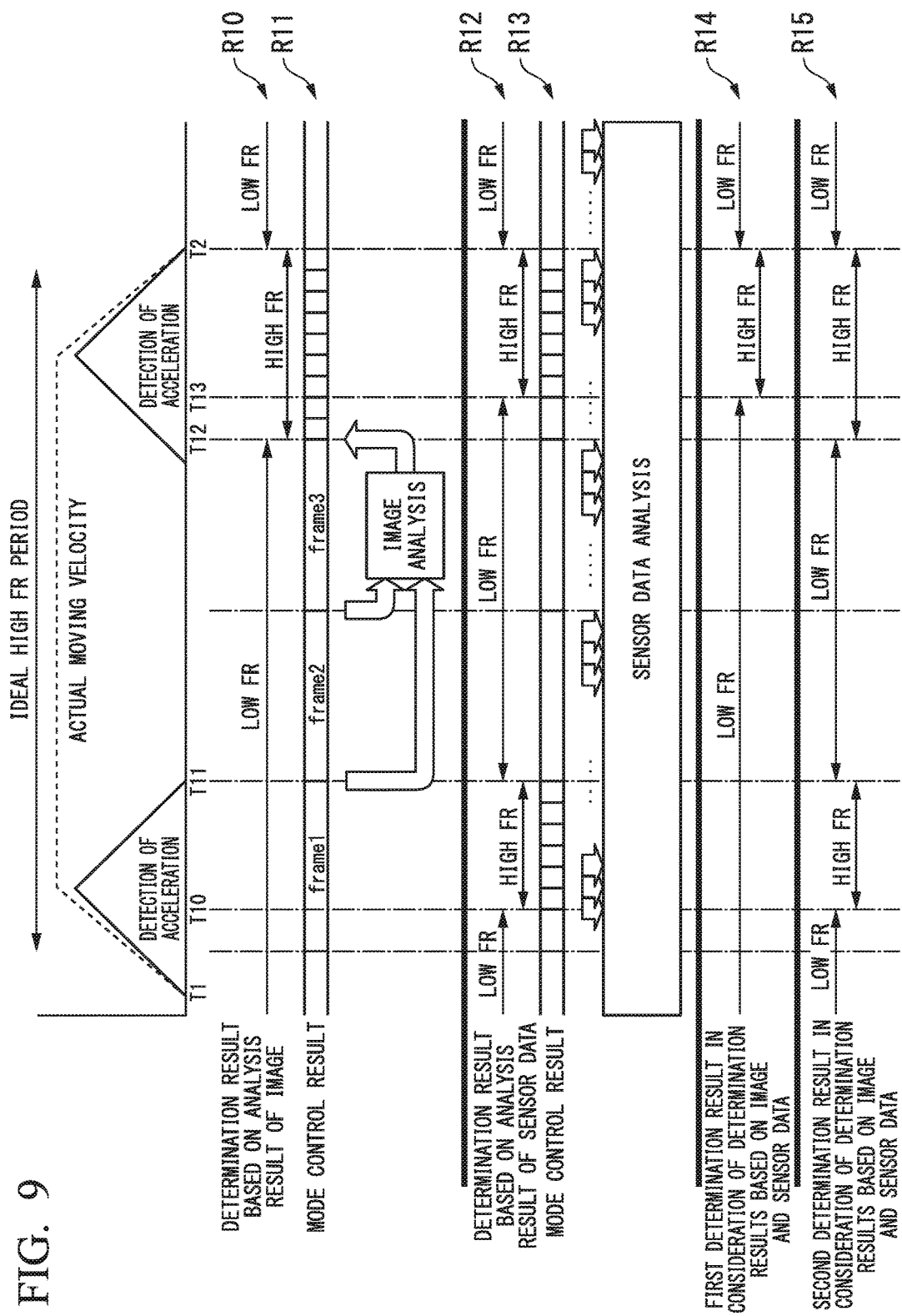
FIG. 9 is a timing chart showing a control method which is compared with the method of controlling the capsule endoscope according to the second embodiment of the present invention.
Figure 10:
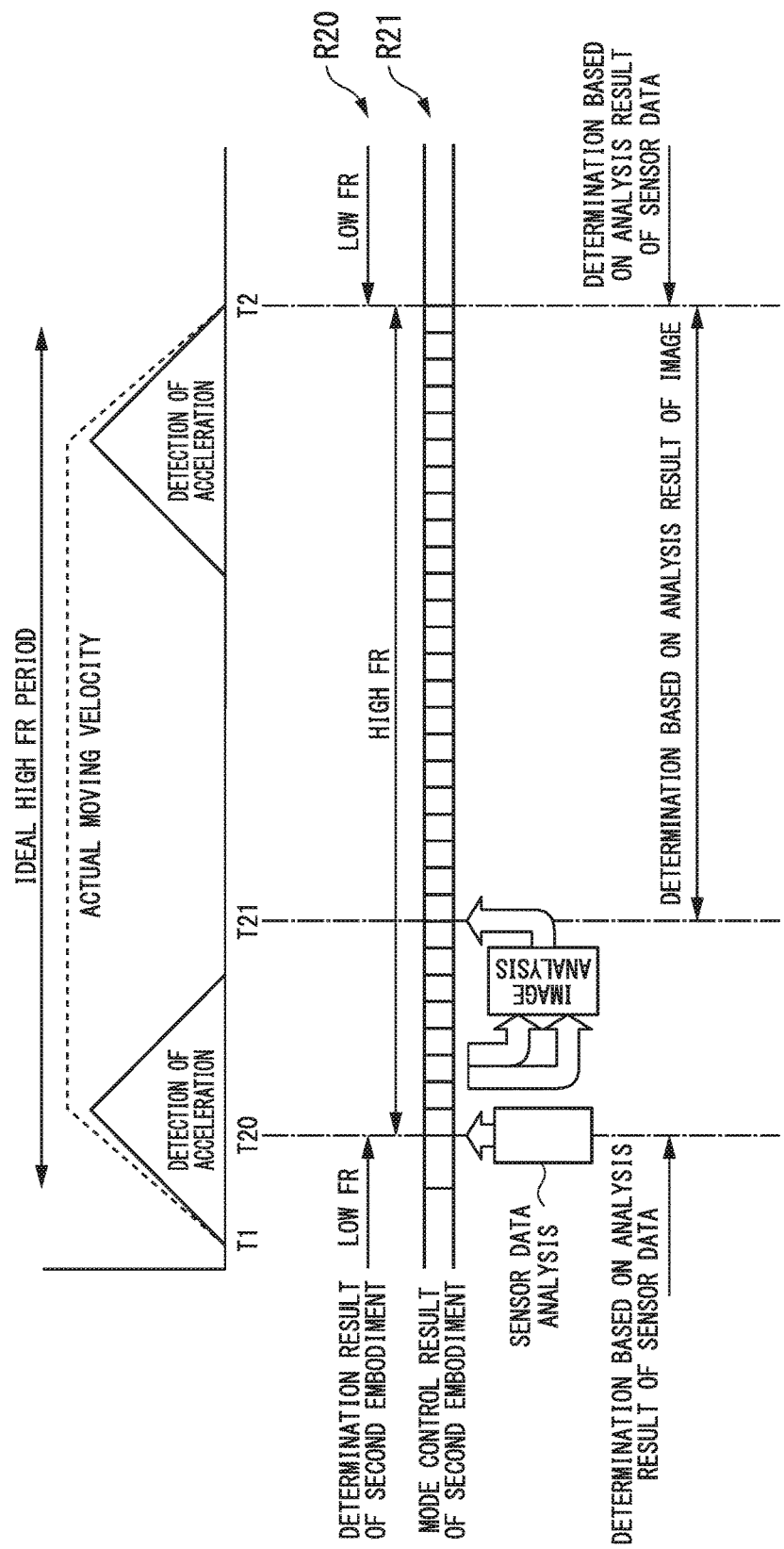
FIG. 10 is a timing chart showing the method of controlling the capsule endoscope according to the second embodiment of the present invention.

FIGS. 9 and 10 show an example of a mode control method. The control method shown in FIG. 10 is based on the process flow shown in FIG. 8. The control method shown in FIG. 9 is compared with the control method shown in FIG. 10 for reference. The control methods shown in FIGS. 9 and 10 will be described below using the capsule endoscope 12.

Time advances toward the right in FIGS. 9 and 10. A "low FR" indicates that the frame rate is low. A "high FR" indicates that the frame rate is high. The frame rate in the first mode is lower than that in the second mode. An "ideal high FR period" is an ideal period in which the mode of the imaging unit 100 is set to the second mode in which the frame rate is high.

The capsule endoscope 12 stops before time T1. At time T1, the mode of the imaging unit 100 is set to the first mode. At time T1, the capsule endoscope 12 starts moving. The moving velocity gradually increases and then the capsule endoscope 12 moves at a constant velocity. Thereafter, the moving velocity gradually decreases. At time T2, the movement of the capsule endoscope 12 ends. The "ideal high FR period" is a period from a time immediately after time T1 at which the capsule endoscope 12 starts moving to a time immediately before time T2 at which movement of the capsule endoscope 12 ends.

In FIG. 9, a mode determination result R10 based on the analysis result of an image and a mode control result R11 based on the determination result R10 are shown. For example, the mode is determined on the basis of an image difference between two successive frames. The image difference is equal to or greater than a predetermined threshold value while the capsule endoscope 12 is moving. Accordingly, it is determined that the mode is to be switched from the first mode to the second mode. When the mode of the imaging unit 100 is set to the first mode, the image acquisition frequency is low. Accordingly, the mode is switched to the second mode at time T12 separated from time T1 at which the capsule endoscope 12 starts moving.

When the moving velocity of the capsule endoscope 12 decreases, the image difference is less than the predetermined threshold value. Accordingly, it is determined that the mode is to be switched from the second mode to the first mode. Since the frame rate in the second mode is higher than that in the first mode, the image acquisition frequency in the second mode is higher. Accordingly, the mode is switched to the first mode at time T2 which is close to the time at which the capsule endoscope 12 stops movement.

When the mode is controlled on the basis of the analysis result of the image, time T12 at which the mode is switched from the first mode to the second mode is greatly separated from time T1 at which the capsule endoscope 12 starts moving. That is, it is difficult to rapidly switch the mode from the first mode to the second mode.

In FIG. 9, a mode determination result R12 based on the analysis result of the sensor data and a mode control result R13 based on the determination result R12 are shown. For example, the sensor data is acceleration data. Immediately after the capsule endoscope 12 starts moving, the acceleration is equal to or greater than a predetermined threshold value due to the movement. Accordingly, it is determined that the mode is to be switched from the first mode to the second mode. The cycle with which the control unit 104 acquires the analysis result of the sensor data is shorter than the cycle with which the control unit 104 acquires the analysis result of the image. Accordingly, the mode is switched to the second mode at time T10 which is close to time T1 at which the capsule endoscope 12 starts moving.

When the velocity of the capsule endoscope 12 is constant, the acceleration is less than the predetermined threshold value. Accordingly, it is determined that the mode is to be switched from the second mode to the first mode. As a result, the mode is switched to the first mode at time T11.

While the velocity of the capsule endoscope 12 is constant, the mode is maintained in the first mode. Thereafter, when the velocity of the capsule endoscope 12 starts decreasing, the acceleration is equal to or greater than the threshold value. Accordingly, it is determined that the mode is to be switched from the first mode to the second mode. As a result, the mode is switched to the second mode at time T13.

When the capsule endoscope 12 stops, the acceleration is less than the predetermined threshold value. Accordingly, it is determined that the mode is to be switched from the second mode to the first mode. As a result, the mode is switched to the first mode at time T2.

When the mode is controlled on the basis of the analysis result of the sensor data, the mode is maintained in the first mode in the period from time T11 to time T13 in which the capsule endoscope 12 moves at a constant velocity. That is, the mode is erroneously switched from the second mode to the first mode.

As described above, when the mode is controlled on the basis of only the analysis result of the image or only the analysis result of the sensor data, it is difficult to control the mode with high accuracy.

In FIG. 9, a first determination result R14 in consideration of the determination result based on the image and the sensor data is shown. When the image difference is less than a predetermined threshold value and the acceleration is less than a predetermined threshold value, it is determined that mode of the imaging unit 100 is set to the first mode. When the image difference is equal to or greater than the predetermined threshold value and the acceleration is equal to or greater than the predetermined threshold value, it is determined that the mode of the imaging unit 100 is set to the second mode.

When the image difference is equal to or greater than the predetermined threshold value and the acceleration is less than the predetermined threshold value, the determination result based on the sensor data has priority. Accordingly, it is determined that the mode of the imaging unit 100 is set to the first mode. When the image difference is less than the predetermined threshold value and the acceleration is equal to or greater than the predetermined threshold value, the determination result based on the image has a priority. Accordingly, it is determined that the mode of the imaging unit 100 is set to the first mode.

The first determination result R14 can be acquired by a logical operation. When the image difference is less than the predetermined threshold value, 0 is assigned to the determination result based on the image. When the image difference is equal to or greater than the predetermined threshold value, 1 is assigned to the determination result based on the image. When the acceleration is less than the predetermined threshold value, 0 is assigned to the determination result based on the sensor data. When the acceleration is equal to or greater than the predetermined threshold value, 1 is assigned to the determination result based on the sensor data. The first determination result R14 is acquired by an AND operation of the value (0 or 1) indicating the determination result based on the image and the value (0 or 1) indicating the determination result based on the sensor data.

When the result of the AND operation is 0, it is determined that the mode of the imaging unit 100 is set to the first mode. When the result of the AND operation is 1, it is determined that the mode of the imaging unit 100 is set to the second mode. When the mode is controlled on the basis of the first determination result R14, it is difficult to rapidly switch the mode from the first mode to the second mode.

In FIG. 9, a second determination result R15 in consideration of the determination result based on the image and the sensor data is shown. When the image difference is less than a predetermined threshold value and the acceleration is less than a predetermined threshold value, it is determined that the mode of the imaging unit 100 is set to the first mode. When the image difference is equal to or greater than the predetermined threshold value and the acceleration is equal to or greater than the predetermined threshold value, it is determined that the mode of the imaging unit 100 is set to the second mode.

When the image difference is equal to or greater than the predetermined threshold value and the acceleration is less than the predetermined threshold value, the determination result based on the image has priority. Accordingly, it is determined that the mode of the imaging unit 100 is set to the second mode. When the image difference is less than the predetermined threshold value and the acceleration is equal to or greater than the predetermined threshold value, the determination result based on the acceleration has a priority. Accordingly, it is determined that the mode of the imaging unit 100 is set to the second mode.

The second determination result R15 can be acquired by a logical operation. When the image difference is less than the predetermined threshold value, 0 is assigned to the determination result based on the image. When the image difference is equal to or greater than the predetermined threshold value, 1 is assigned to the determination result based on the image. When the acceleration is less than the predetermined threshold value, 0 is assigned to the determination result based on the sensor data. When the acceleration is equal to or greater than the predetermined threshold value, 1 is assigned to the determination result based on the sensor data. The second determination result R15 is acquired by an OR operation of the value (0 or 1) indicating the determination result based on the image and the value (0 or 1) indicating the determination result based on the sensor data.

When the result of the OR operation is 0, it is determined that the mode of the imaging unit 100 is set to the first mode. When the result of the OR operation is 1, it is determined that the mode of the imaging unit 100 is set to the second mode. When the mode is controlled on the basis of the second determination result R15, the mode is erroneously switched from the second mode to the first mode while the capsule endoscope 12 is moving.

As represented by the first determination result R14 and the second determination result R15 in FIG. 9, it can be seen that the mode cannot be suitably controlled only by simply combining the determination result based on the image and the determination result based on the sensor data.

In FIG. 10, a mode determination result R20 based on the control method shown in FIG. 8 and a mode control result R21 based on the determination result R20 are shown. For example, the sensor data is acceleration data. Immediately after the capsule endoscope 12 starts moving, the acceleration is equal to or greater than a predetermined threshold value due to the movement. Accordingly, it is determined that the mode is to be switched from the first mode to the second mode. The cycle with which the control unit 104 acquires the analysis result of the sensor data is shorter than the cycle with which the control unit 104 acquires the analysis result of the image. Accordingly, the mode is switched to the second mode at time T20 which is close to time T1 at which the capsule endoscope 12 starts moving.

After time T20, the mode is determined on the basis of the analysis result of the image. Since a time is required for the image analysis, the mode is maintained in the second mode until the analysis result of the image acquired by an imaging operation which is performed after time T20 is acquired. The first analysis result of the image acquired by the imaging operation which is performed after time T20 is acquired at time T21. After time T21, it is possible to determine the mode on the basis of the analysis result of the image.

While the velocity of the capsule endoscope 12 is constant, the mode is maintained in the first mode. When the moving velocity of the capsule endoscope 12 decreases, the image difference is less than the predetermined threshold value. Accordingly, it is determined that the mode is to be switched from the second mode to the first mode. Since the frame rate in the second mode is higher than that in the first mode, the image acquisition frequency in the second mode is high. Accordingly, the mode is switched to the first mode at time T2 which is close to the time at which the movement of the capsule endoscope 12 stops.

When the mode is controlled using the control method shown in FIG. 10, the mode is set to the second mode from time T20 to time T2. Accordingly, it is possible to control the mode more accurately than with the control method shown in FIG. 9.

In FIG. 10, the cycle in which the control unit 104 acquires the analysis result of the image when the mode of imaging unit 100 is set to the second mode is shorter than the cycle in which the control unit 104 acquires the analysis result of the image when the mode of the imaging unit 100 is set to the first mode. However, the cycle in which the control unit 104 acquires the analysis result of the image when the mode of the imaging unit 100 is set to the second mode may be equal to the cycle in which the control unit 104 acquires the analysis result of the image when the mode of the imaging unit 100 is set to the first mode. In FIG. 10, it is possible to maintain the mode as the second mode when the velocity of the capsule endoscope 12 is constant without depending on the cycle with which the control unit 104 acquires the analysis result of the image. That is, it is possible to control the mode more accurately than with the mode control method based on the second determination result R15 in FIG. 9.

The capsule endoscope 11 shown in FIG. 4 may include a data acquiring unit 101a instead of the data acquiring unit 101. In the method of controlling the capsule endoscope 11 shown in FIG. 5, the data other than an image may be sensor data.

In the second embodiment, when the mode of the imaging unit 100 is set to the first mode, the mode of the imaging unit 100 is switched to the second mode on the basis of the analysis result of the sensor data. When the mode of the imaging unit 100 is set to the second mode, the mode of the imaging unit 100 is switched to the first mode on the basis of the analysis result of the image. Accordingly, it is possible to control the imaging mode more accurately.

In the second embodiment, since the sensor data can be rapidly acquired, it is possible to more rapidly switch the mode from the first mode to the second mode. It is also possible to determine whether to switch the mode from the second to the first mode with high accuracy on the basis of the analysis result of the image.

(Third Embodiment)

A third embodiment of the present invention will be described below using the capsule endoscope 12 shown in FIG. 6. In the third embodiment, similarly to the second embodiment, the imaging frame rate in the first mode is lower than the imaging frame rate in the second mode.

In a first example of the third embodiment, the mode of the imaging unit 100 is set to any one of a first mode, a second mode, and a third mode. The imaging frame rate in the third mode is higher than the imaging frame rate in the second mode. When the mode of the imaging unit 100 is set to the second mode, the control unit 104 switches the mode of the imaging unit 100 to the first mode or the third on the basis of the analysis result of the image. When the mode of the imaging unit 100 is set to the third mode, the control unit 104 switches the mode of the imaging unit 100 to the first mode or the second mode on the basis of the analysis result of the image.

In a second example of the third embodiment, the mode of the imaging unit 100 is set to any one of a first mode, a second mode, and a fourth mode. The imaging frame rate in the fourth mode is lower than the imaging frame rate in the first mode. When the mode of the imaging unit 100 is set to the fourth mode, the control unit 104 switches the mode of the imaging unit 100 to the first mode on the basis of the analysis result of the data. When the mode of the imaging unit 100 is set to the first mode, the control unit 104 switches the mode of the imaging unit 100 to the second mode or the fourth mode on the basis of the analysis result of the data.

An example in which the mode of the imaging unit 100 is set to any one of the first mode, the second mode, the third mode, and the fourth mode will be described below.

Figure 11:
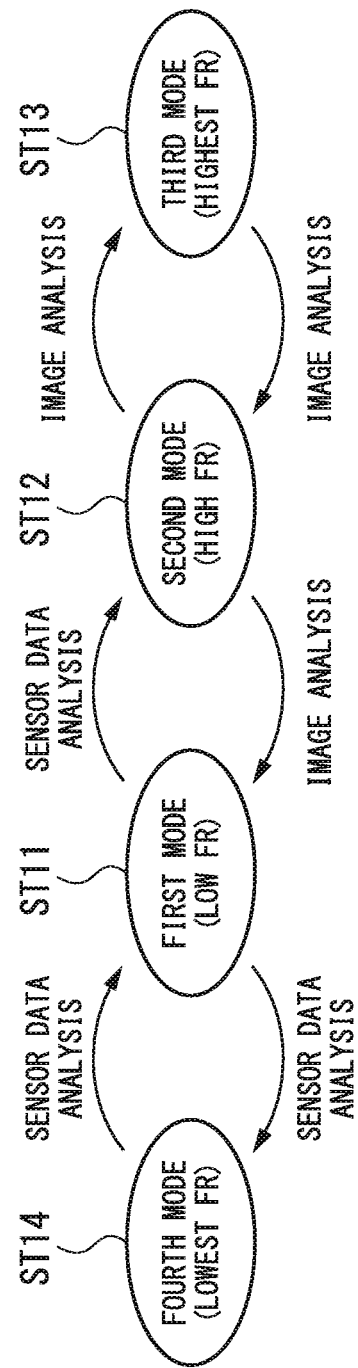
FIG. 11 is a reference diagram showing a state transition of an imaging unit in a third embodiment of the present invention.

FIG. 11 shows a state transition of the imaging unit 100. A state transition between the state ST11 in which the mode of the imaging unit 100 is set to the first mode and the state ST12 in which the mode of the imaging unit 100 is set to the second mode is the same as the state transition in the second embodiment.

In the state ST12 in which the mode of the imaging unit 100 is set to the second mode, the control unit 104 determines the mode on the basis of the analysis result of the image. For example, when the image variation at a plurality of times is equal to or greater than a predetermined threshold value, the control unit 104 determines that the mode of the imaging unit 100 is to be switched to the third mode. When the image variation at a plurality of times is less than a predetermined threshold value, the control unit 104 determines that the mode of the imaging unit 100 is to be switched to the first mode.

When the control unit 104 determines that the mode of the imaging unit 100 is to be switched to the third mode, the control unit 104 switches the mode of the imaging unit 100 to the third mode. As a result, the imaging unit 100 is in a state ST13 in which the third mode is set.

In the state ST13, the control unit 104 determines the mode on the basis of the analysis result of the image. For example, when the image variation at a plurality of times is equal to or greater than a predetermined threshold value, the control unit 104 determines that the mode of the imaging unit 100 is not to be switched. When the image variation at a plurality of times is less than a predetermined threshold value, the control unit 104 determines that the mode of the imaging unit 100 is to be switched to the second mode.

When the control unit 104 determines that the mode of the imaging unit 100 is to be switched to the second mode, the control unit 104 switches the mode of the imaging unit 100 to the second mode. As a result, the imaging unit 100 is in the state ST12 in which the second mode is set. The predetermined threshold value in the state ST13 has only to be equal to or greater than the predetermined threshold value in the state ST12.

For example, when the motion of the capsule endoscope 12 increases in the state ST12 in which the capsule endoscope 12 is moving, the mode of the imaging unit 100 is set to the third mode.

In the state ST13, when the image variation at a plurality of times is less than the predetermined threshold value, the mode of the imaging unit 100 may be switched to the first mode. Alternatively, when a first threshold value and a second threshold value greater than the first threshold value are set and the image variation at a plurality of times is less than the first threshold value, the mode of the imaging unit 100 may be switched to the first mode. When the image variation at a plurality of times is equal to or greater than the first threshold value and less than the second threshold value, the mode of the imaging unit 100 may be switched to the second mode. When the image variation at a plurality of times is equal to or greater than the second threshold value, the mode of the imaging unit 100 may be maintained in the third mode.

In the state ST11 in which the mode of the imaging unit 100 is set to the first mode, the control unit 104 determines the mode on the basis of the analysis result of the sensor data. For example, when the sensor data or the variation thereof is equal to or greater than a predetermined threshold value, the control unit 104 determines that the mode of the imaging unit 100 is to be switched to the second mode. When the sensor data or the variation thereof is less than the predetermined threshold value, the control unit 104 determines that the mode of the imaging unit 100 is to be switched to the fourth mode.

When the control unit 104 determines that the mode of the imaging unit 100 is to be switched to the fourth mode, the control unit 104 switches the mode of the imaging unit 100 to the fourth mode. As a result, the imaging unit 100 is in the state ST14 in which the fourth mode is set.

In the state ST14, the control unit 104 determines the mode on the basis of the analysis result of the data. For example, when the sensor data or the variation thereof is equal to or greater than the predetermined threshold value, the control unit 104 determines that the mode of the imaging unit 100 is to be switched to the first mode. When the sensor data or the variation thereof is less than the predetermined threshold value, the control unit 104 determines that the mode of the imaging unit 100 is not to be switched.

When the control unit 104 determines that the mode of the imaging unit 100 is to be switched to the first mode, the control unit 104 switches the mode of the imaging unit 100 to the first mode. As a result, the imaging unit 100 is in a state ST11 in which the first mode is set. The predetermined threshold value in the state ST14 has only to be equal to or less than the predetermined threshold value in the state ST11.

For example, when the motion of the capsule endoscope 12 becomes slower in the state ST11 in which the capsule endoscope 12 is moving slowly, the mode of the imaging unit 100 is set to the fourth mode.

In the state ST11, when the image variation at a plurality of times is less than the predetermined threshold value, the mode of the imaging unit 100 may be switched to the fourth mode.

When the sensor data is acceleration data, the determination in the state ST11 may include determination of an acceleration direction. For example, when acceleration having a direction in which the movement of the capsule endoscope 12 becomes faster is detected, the mode may be switched to the first mode. When acceleration having a direction in which the movement of the capsule endoscope 12 becomes slower is detected, the mode may be switched to the fourth mode. Similarly, when the sensor data is angular velocity data or magnetic data, the determination in the state ST11 may include determination of an angular velocity direction or a magnetism direction.

Figure 12:
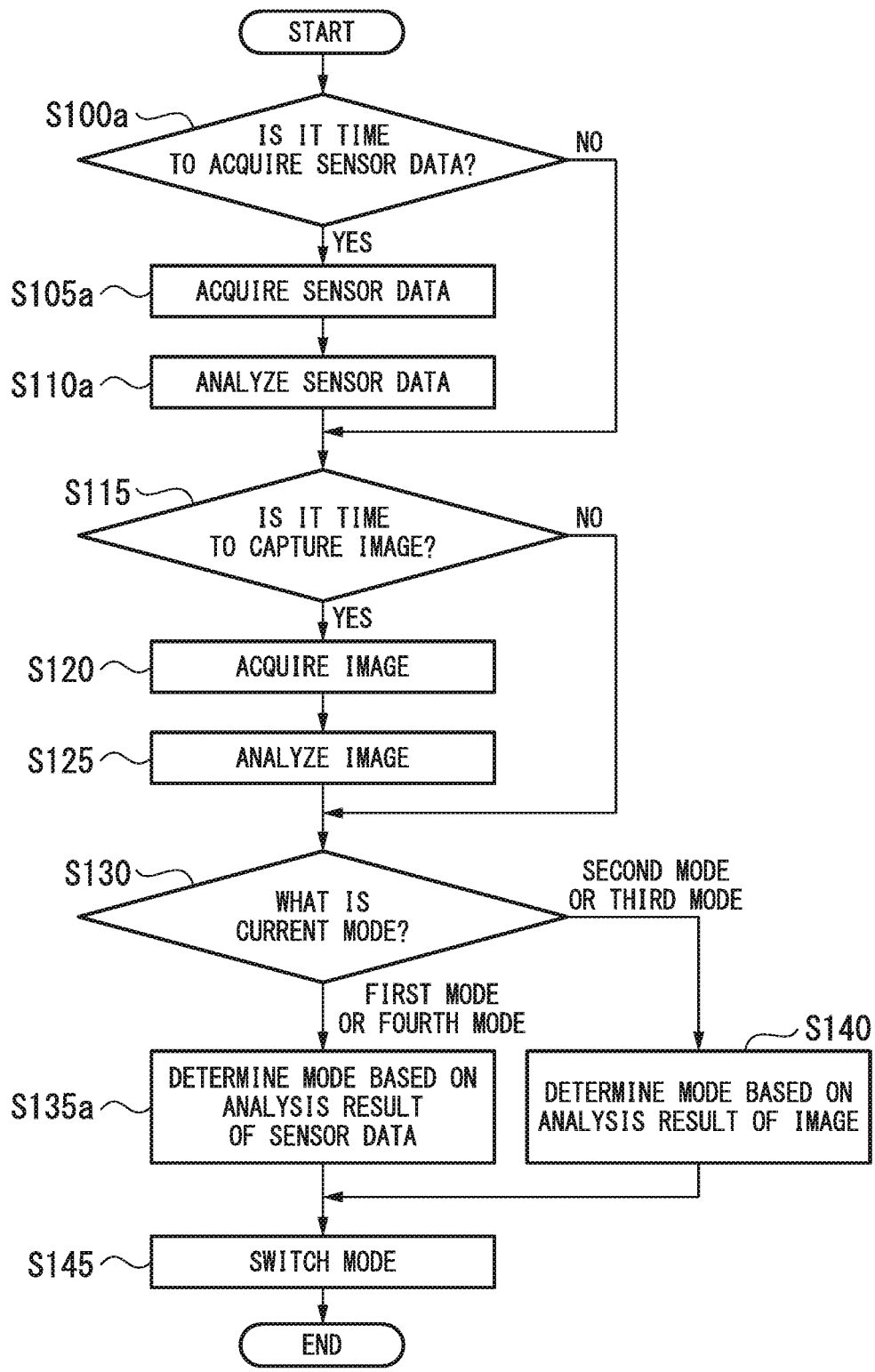
FIG. 12 is a flowchart showing a method of controlling the capsule endoscope according to the third embodiment of the present invention.

FIG. 12 shows a method of controlling the capsule endoscope 12. A difference of the process flow shown in FIG. 12 from the process flow shown in FIG. 8 will be described below.

After an image is analyzed in Step S125, the process flow branches depending on the mode of the imaging unit 100 (Step S130). When the mode of the imaging unit 100 is the first mode or the fourth mode, the control unit 104 determines the mode of the imaging unit 100 on the basis of the analysis result of the sensor data (Step S135). On the other than, when the mode of the imaging unit 100 is the second mode or the third mode, the control unit 104 determines the mode of the imaging unit 100 on the basis of the analysis result of the image (Step S140)

The processes other than those described above are the same as in the processes shown in FIG. 8.

In the third embodiment, the third mode of which the frame rate is higher than that in the second mode can be set in the imaging unit 100. In the third mode, it is possible to further reduce an imaging error of a subject.

In the third embodiment, the fourth mode of which the frame rate is lower than that in the first mode can be set in the imaging unit 100. When the mode of the imaging unit 100 is set to the fourth mode, the image acquisition frequency is lower than that when the mode of the imaging unit 100 is set to the first mode. Accordingly, in the fourth mode, it is possible to more reduce power consumption than in the first mode. When the mode of the imaging unit 100 is set to the fourth mode, it is possible to rapidly switch the mode from the fourth mode to the first mode on the basis of the analysis result of the sensor data.

(Fourth Embodiment)

Figure 13:
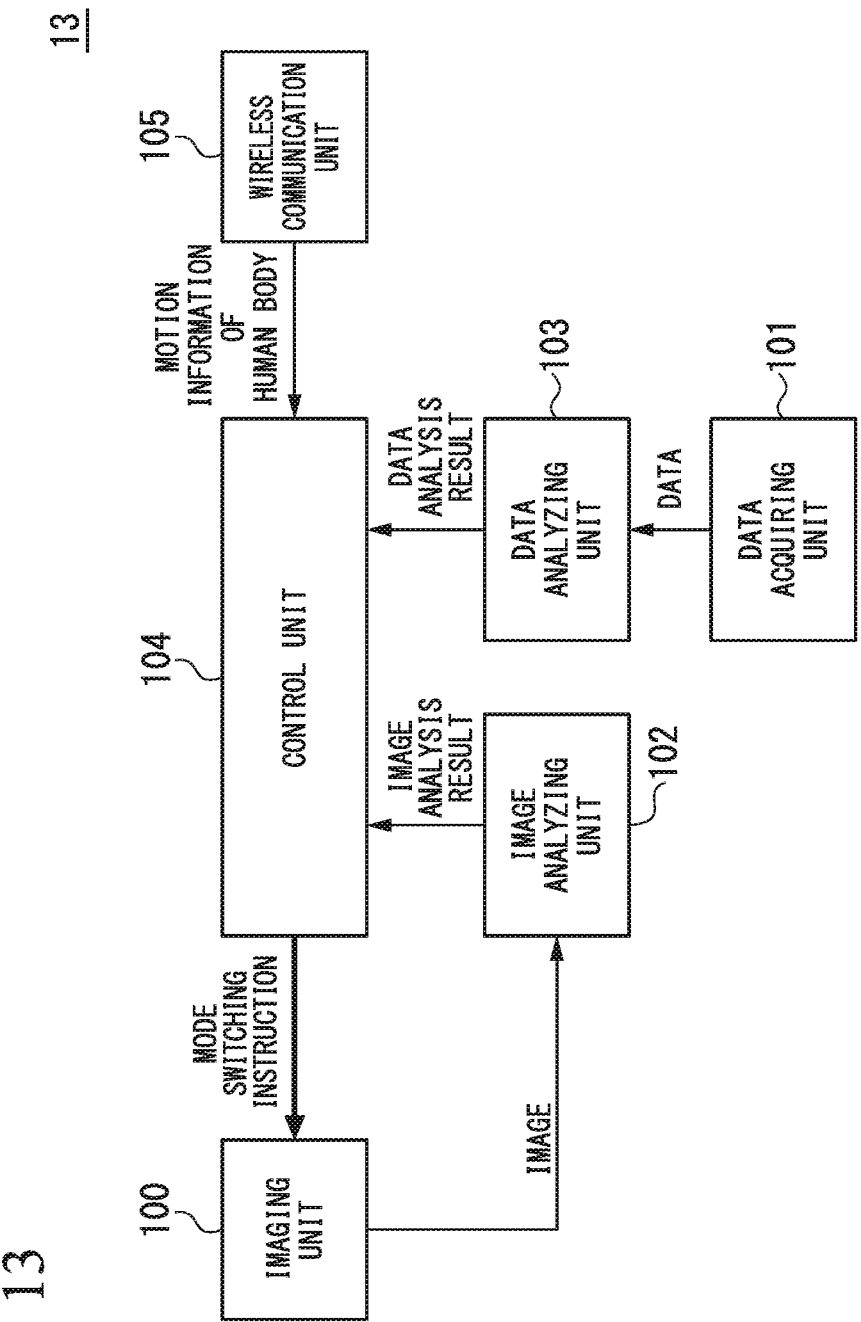
FIG. 13 is a block diagram showing a configuration of a capsule endoscope according to a fourth embodiment of the present invention.

FIG. 13 shows a configuration of a capsule endoscope 13 according to a fourth embodiment of the present invention. As shown in FIG. 13, the capsule endoscope 13 includes an imaging unit 100, a data acquiring unit 101, an image analyzing unit 102, a data analyzing unit 103, a control unit 104, and a wireless communication unit 105 (a first wireless communication unit). In the fourth embodiment, similarly to the second embodiment, the imaging frame rate in the first mode is lower than the imaging frame rate in the second mode.

The imaging unit 100 is the same as the imaging unit 100 in the capsule endoscope 10 shown in FIG. 1. The data acquiring unit 101 is the same as the data acquiring unit 101 in the capsule endoscope 10 shown in FIG. 1. The data acquiring unit 101 may be the sensor 101a in the capsule endoscope 12 shown in FIG. 6. The image analyzing unit 102 is the same as the image analyzing unit 102 in the capsule endoscope 10 shown in FIG. 1. The data analyzing unit 103 is the same as the data analyzing unit 103 in the capsule endoscope 10 shown in FIG. 1.

The wireless communication unit 105 wirelessly transmits the image acquired by the imaging unit 100 to a receiver device. The wireless communication unit 105 wirelessly receives motion information for identifying a first case in which a motion of a human body into which the capsule endoscope 13 is inserted is relatively small and a second case in which the motion of the human body is relatively large from the receiver device. Only when the mode of the imaging unit 100 is set to the first mode and the motion of the human body is relatively small, the control unit 104 switches the mode of the imaging unit 100 to the second mode on the basis of the analysis result of the data.

The receiver device detects the motion of the human body into which the capsule endoscope 13 is inserted. The receiver device analyzes the detected motion and generates the motion information on the basis of the analysis result of the motion. The receiver device wirelessly transmits the generated motion information to the capsule endoscope 13.

When the capsule endoscope 13 stops relative to the human body but the human body moves, the motion of the capsule endoscope 13 may be detected on the basis of the data acquired by the data acquiring unit 101. In this case, control based on the motion information is performed so as not to erroneously switch the mode.

For example, when the mode of the imaging unit 100 is set to the first mode and the motion information indicates the first case, the control unit 104 switches the mode to the second mode on the basis of the analysis result of the data. When mode of the imaging unit 100 is set to the first mode and the motion information indicates the second case, the control unit 104 may maintain the mode in the first mode.

Only when the mode of the imaging unit 100 is set to the first mode and the motion information indicating the first case is received, the control unit 104 may switch the mode to the second mode on the basis of the analysis result of the data. When the mode of the imaging unit 100 is set to the first mode and the motion information is not received, the control unit 104 maintains the mode in the first mode.

The movement of the capsule endoscope 13 relative to the human body can be detected on the basis of the analysis result of the image regardless of the motion of the human body. Accordingly, when the mode of the imaging unit 100 is set to the second mode, the control unit 104 controls the mode on the basis of the analysis result of the image regardless of the motion information.

When the mode of the imaging unit 100 is set to the first mode and the motion of the human body is relatively large, the control unit 104 may switch the mode to the second mode on the basis of the analysis result of the image.

Figure 14:
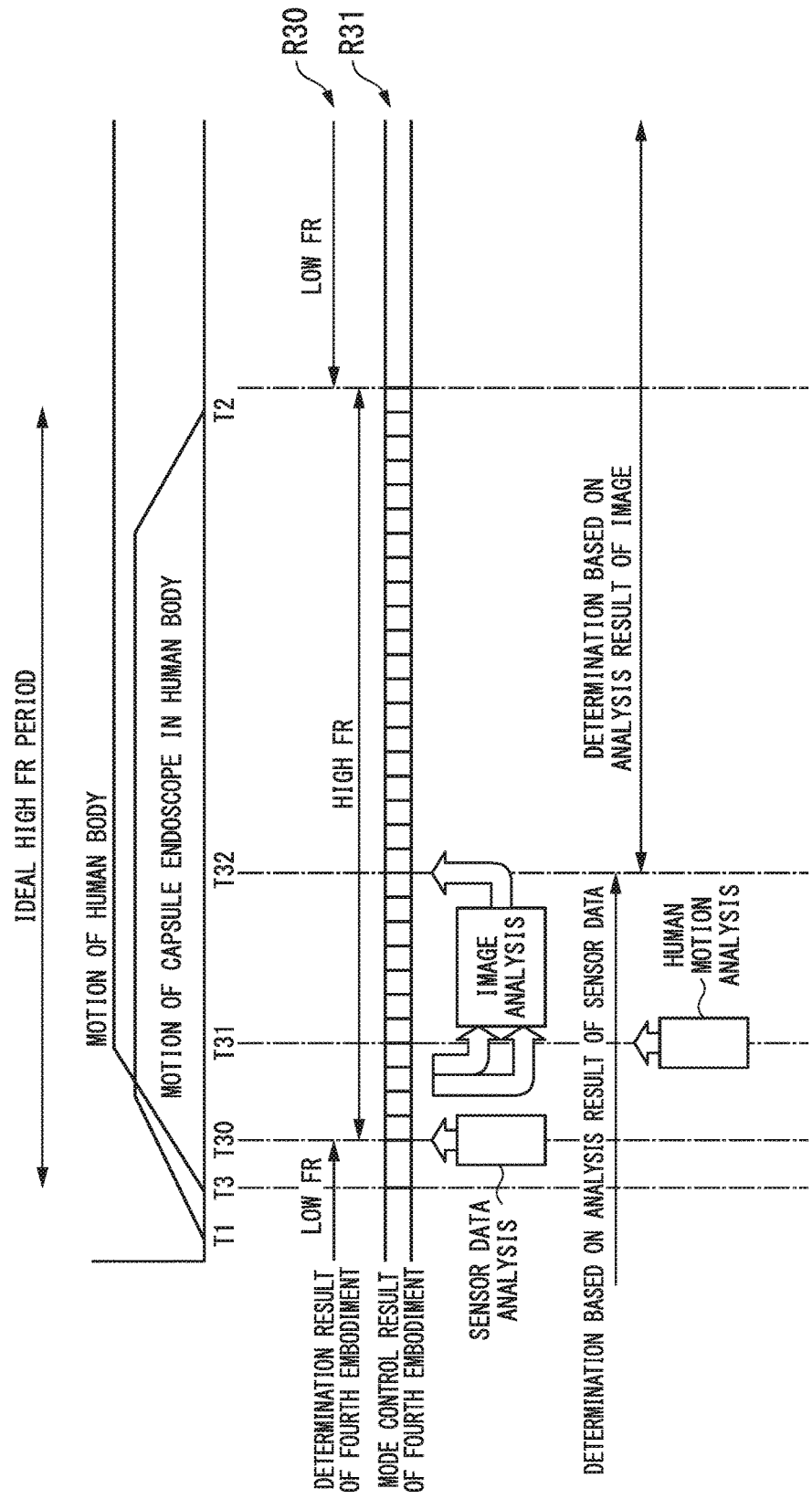
FIG. 14 is a timing chart showing the method of controlling the capsule endoscope according to the fourth embodiment of the present invention.

FIG. 14 shows an example of a mode control method. Time advances toward the right in FIG. 14. A "low FR" indicates that the frame rate is low. A "high FR" indicates that the frame rate is high. The frame rate in the first mode is lower than that in the second mode. An "ideal high FR period" is an ideal period in which the second mode in which the frame rate of the imaging unit 100 is high.

The capsule endoscope 13 stops before time T1. At time T1, the mode of the imaging unit 100 is set to the first mode. At time T1, the capsule endoscope 13 starts movement. The moving velocity gradually increases and then the capsule endoscope 13 moves at a constant velocity. Thereafter, the moving velocity gradually decreases. At time T2, the movement of the capsule endoscope 13 ends. The "ideal high FR period" is a period from a time immediately after time T1 at which the capsule endoscope 13 starts movement to a time immediately before time T2 at which movement of the capsule endoscope 13 ends. At time T3 immediately after the capsule endoscope 13 starts movement, the human body into which the capsule endoscope 13 is inserted starts movement.

In FIG. 14, a mode determination result R30 based on the control method according to the fourth embodiment and a mode control result R31 based on the determination result R30 are shown. For example, the data is acceleration data. Immediately after the capsule endoscope 13 starts movement, the acceleration is equal to or greater than a predetermined threshold value due to the movement.

Up to time T30, the receiver device wirelessly transmits the motion information indicating the first case in which the motion of the human body is relatively small to the capsule endoscope 13. The wireless communication unit 105 receives the motion information. The received motion information is output to the control unit 104. When the motion information indicates the first case and the acceleration is equal to or greater than the predetermined threshold value, it is determined that the mode is switched from the first mode to the second mode. As a result, the mode is switched to the second mode at time t30 which is close to time T1 at which the capsule endoscope 13 starts movement.

After time T30, the mode is determined on the basis of the analysis result of the image. Since a time is required for the image analysis, the mode is maintained in the second mode until the analysis result of the image acquired by an imaging operation which is performed after time T30. The first analysis result of the image acquired by the imaging operation which is performed after time T30 is acquired at time T32. After time T32, it is possible to determine the mode on the basis of the analysis result of the image.

At time T31 between time T30 and time T32, the receiver device detects the motion of the human body which is equal to or greater than a predetermined threshold value. The receiver device wirelessly transmits the motion information indicating the second case in which the motion of the human body is relatively large to the capsule endoscope 13. The wireless communication unit 105 receives the motion information. The received motion information is output to the control unit 104.

While the velocity of the capsule endoscope 13 is constant, the mode is maintained in the first mode. When the moving velocity of the capsule endoscope 13 decreases, the image difference is less than the predetermined threshold value. Accordingly, it is determined that the mode is switched from the second mode to the first mode. Since the frame rate in the second mode is higher than that in the first mode, the image acquisition frequency in the second mode is high. Accordingly, the mode is switched to the first mode at time T2 which is close to the time at which the movement of the capsule endoscope 13 stops.

Since the motion information indicating the second case is received, the control unit 104 switches the mode to the second mode on the basis of the analysis result of the image without depending on the analysis result of the data after the mode is switched to the first mode. Accordingly, after time T2, the human body moves, but the mode is maintained in the first mode.

In the fourth embodiment, the capsule endoscope 13 controls the mode in consideration of the motion of the human body. Accordingly, when the motion of the human body is relatively large and the motion of the capsule endoscope is relatively small, it is possible to prevent the second mode having a higher frame rate than that in the first mode form being set in the imaging unit 100. That is, it is possible to control the mode more accurately.

(Fifth Embodiment)

Figure 15:
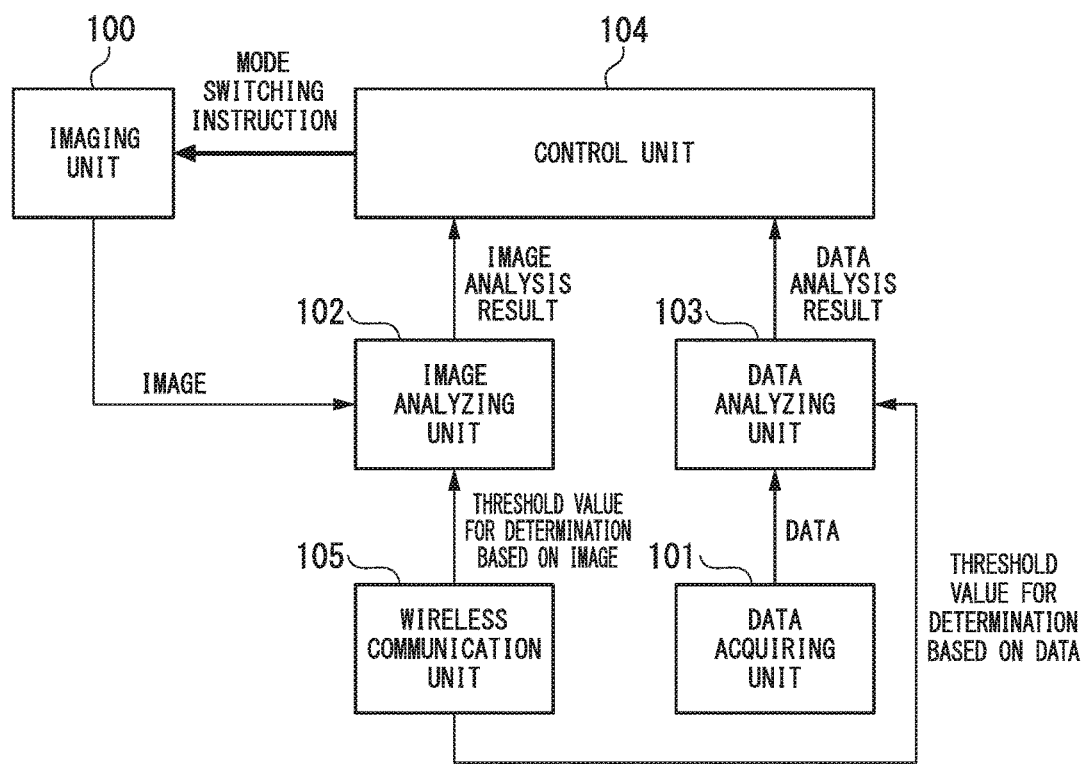
FIG. 15 is a block diagram showing a configuration of a capsule endoscope according to a fifth embodiment of the present invention.

FIG. 15 shows a configuration of a capsule endoscope 14 according to a fifth embodiment of the present invention. As shown in FIG. 15, the capsule endoscope 14 includes an imaging unit 100, a data acquiring unit 101, an image analyzing unit 102, a data analyzing unit 103, a control unit 104, and a wireless communication unit 105 (a first wireless communication unit). In the fifth embodiment, similarly to the second embodiment, the imaging frame rate in the first mode is lower than the imaging frame rate in the second mode.

The imaging unit 100 is the same as the imaging unit 100 in the capsule endoscope 10 shown in FIG. 1. The data acquiring unit 101 is the same as the data acquiring unit 101 in the capsule endoscope 10 shown in FIG. 1. The data acquiring unit 101 may be the sensor 101a in the capsule endoscope 12 shown in FIG. 6. The image analyzing unit 102 is the same as the image analyzing unit 102 in the capsule endoscope 10 shown in FIG. 1. The data analyzing unit 103 is the same as the data analyzing unit 103 in the capsule endoscope 10 shown in FIG. 1.

The wireless communication unit 105 wirelessly transmits the image acquired by the imaging unit 100 to a receiver device. The wireless communication unit 105 wirelessly receives threshold values from the receiver device. The threshold values include a threshold value for determining the mode using the image, that is, determining the mode on the basis of the analysis result of the image and a threshold value for determining the mode using the data, that is, determining the mode on the basis of the analysis result of the data.

The receiver device selects one of a plurality of threshold values depending on a remaining capacity of a battery of the capsule endoscope 14. For example, the receiver device includes a table in which the remaining capacity of the battery of the capsule endoscope 14 is correlated with the threshold value. In the table, the remaining capacity of the battery of the capsule endoscope 14 is correlated with the threshold value for determining the mode on the basis of the analysis result of the image and the threshold value for determining the mode on the basis of the analysis result of the data.

The smaller the remaining capacity of the battery becomes, the greater the threshold value becomes. That is, the smaller the remaining capacity of the battery, the easier the setting of the first mode in the imaging unit 100 becomes. The receiver device estimates the remaining capacity of the battery of the capsule endoscope 14. The receiver device selects the threshold value corresponding to the estimated remaining capacity from the table. The receiver device wirelessly transmits the selected threshold value to the capsule endoscope 14.

The receiver device estimates the remaining capacity of the battery of the capsule endoscope 14 using the following method. For example, the receiver device estimates the remaining capacity of the battery of the capsule endoscope 14 on the basis of the number of images captured by the imaging unit 100. The receiver device may estimate the remaining capacity of the battery of the capsule endoscope 14 on the basis of the time elapsing after the motion of the capsule endoscope 14 starts. The receiver device may estimate the remaining capacity of the battery of the capsule endoscope 14 on the basis of a current position (such as a specific organ) of the capsule endoscope 14. For example, the receiver device detects the current position of the capsule endoscope 14 by analyzing the image received from the capsule endoscope 14. The receiver device may receive information indicating the remaining capacity of the battery of the capsule endoscope 14 from the capsule endoscope 14.

The threshold value for determination of the mode based on the analysis result of the image, which is received by the wireless communication unit 105, is output to the image analyzing unit 102. The threshold value for determination of the mode based on the analysis result of the data, which is received by the wireless communication unit 105, is output to the data analyzing unit 103. The image analyzing unit 102 compares the image output from the imaging unit 100 with the threshold value output from the wireless communication unit 105. The data analyzing unit 103 compares the data output from the data acquiring unit 101 with the threshold value output from the wireless communication unit 105.

The receiver device may transmit information (such as IDs of the threshold values) for designating the threshold value instead of transmitting the threshold values. The wireless communication unit 105 wirelessly receives the information designating the threshold values. The image analyzing unit 102 and the data analyzing unit 103 store a plurality of threshold values. The image analyzing unit 102 and the data analyzing unit 103 select the threshold values designated by the information which has been received by the wireless communication unit 105.

In the fifth embodiment, when the remaining capacity of the battery of the capsule endoscope 14 is small, the image analyzing unit 102 and the data analyzing unit 103 are set to a smaller threshold value. Accordingly, when the mode of the imaging unit 100 is set to the first mode, it is difficult to switch the mode to the second mode. When the mode of the imaging unit 100 is set to the second mode, it is easy to switch the mode to the first mode. Accordingly, it is possible to reduce power consumption of the capsule endoscope 14.

(Sixth Embodiment)

Figure 16:
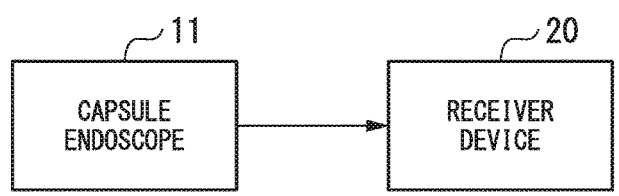
FIG. 16 is a block diagram showing a configuration of a capsule endoscope according to a sixth embodiment of the present invention.

FIG. 16 shows a configuration of a capsule endoscope system 1 according to a sixth embodiment of the present invention. As shown in FIG. 16, the capsule endoscope system 1 includes a capsule endoscope 11 and a receiver device 20. The configuration of the capsule endoscope 11 is the same as shown in FIG. 4.

Figure 17:
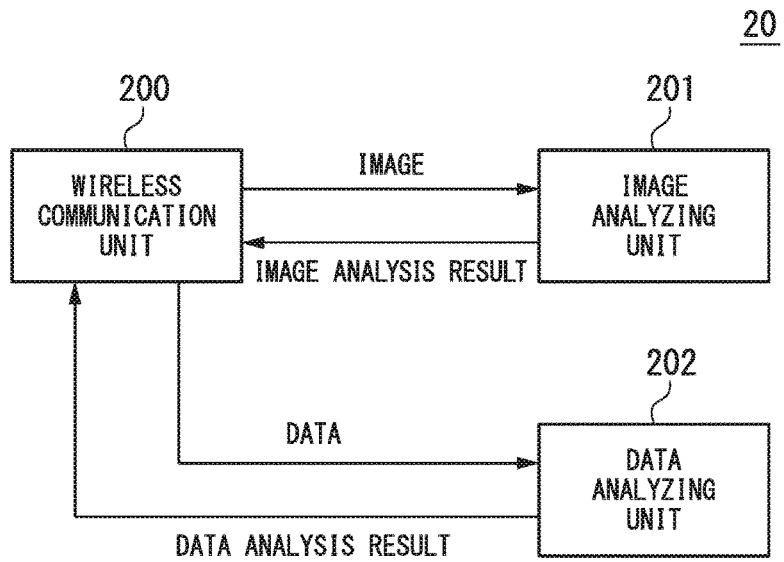
FIG. 17 is a block diagram showing a configuration of a receiver device according to the sixth embodiment of the present invention.

FIG. 17 shows a configuration of the receiver device 20. As shown in FIG. 17, the receiver device 20 includes a wireless communication unit 200 (a second wireless communication unit), an image analyzing unit 201, and a data analyzing unit 202.

The wireless communication unit 200 wirelessly receives the image and the data other than the image which are transmitted from the capsule endoscope 11. The wireless communication unit 200 wirelessly transmits the analysis result of the image and the analysis result of the data to the capsule endoscope 11. The image received by the wireless communication unit 200 is output to the image analyzing unit 201. The data received by the wireless communication unit 200 is output to the data analyzing unit 202.

The image analyzing unit 201 analyzes the image. The analysis result of the image is output to the wireless communication unit 200. The data analyzing unit 202 analyzes the data. The analysis result of the data is output to the wireless communication unit 200.

The receiver device 20 may include a display unit configured to display the image received by the wireless communication unit 200. As shown in FIG. 1, the capsule endoscope 10 can include the image analyzing unit 102 and the data analyzing unit 103. Accordingly, the image analyzing unit 201 and the data analyzing unit 202 are not essential for the receiver device 20. The receiver device 20 may include one of the image analyzing unit 201 and the data analyzing unit 202 and the capsule endoscope 11 may include the other of the image analyzing unit 201 and the data analyzing unit 202.

According to the sixth embodiment, the capsule endoscope system 1 including the capsule endoscope 11 and the receiver device 20 is provided. The capsule endoscope 11 includes the imaging unit 100 configured to image a subject and to acquire an image of the subject in a state in which it is set to any one of the first mode and the second mode, the data acquiring unit 101 configured to acquire data other than an image, the control unit 104 configured to switch the mode of the imaging unit 100 between the first mode and the second mode on the basis of an analysis result of the image and an analysis result of the data, and the first wireless communication unit (the wireless communication unit 105) configured to transmit the image acquired by the imaging unit 100 to the receiver device 20. The control unit 104 switches the mode of the imaging unit 100 to the second mode on the basis of the analysis result of the data when the mode of the imaging unit 100 is set to the first mode, and switches the mode of the imaging unit 100 to the first mode on the basis of the analysis result of the image when the mode of the imaging unit 100 is set to the second mode. The receiver device 20 includes the second wireless communication unit (the wireless communication unit 200) configured to receive the image transmitted from the capsule endoscope 11.

In the sixth embodiment, when the mode of the imaging unit 100 is set to the first mode, the mode of the imaging unit 100 is switched to the second mode on the basis of the analysis result of the data. When the mode of the imaging unit 100 is set to the second mode, the mode of the imaging unit 100 is switched to the first mode on the basis of the analysis result of the image. Accordingly, it is possible to control the imaging mode more accurately.

(Seventh Embodiment)

In a seventh embodiment of the present invention, the capsule endoscope 11 in the capsule endoscope system 1 shown in FIG. 16 is replaced with the capsule endoscope 13 shown in FIG. 13. The receiver device 20 is replaced with a receiver device 21 shown in FIG. 18.

Figure 18:
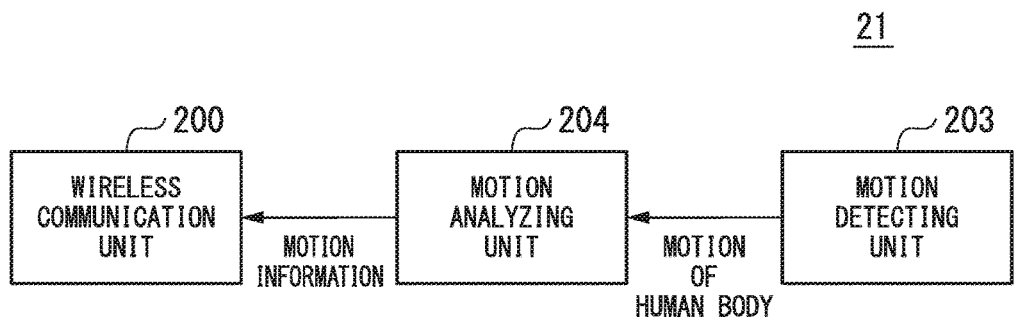
FIG. 18 is a block diagram showing a configuration of a receiver device according to a seventh embodiment of the present invention.

FIG. 18 shows a configuration of the receiver device 21. As shown in FIG. 18, the receiver device 21 includes a wireless communication unit 200 (a second wireless communication unit), a motion detecting unit 203, and a motion analyzing unit 204.

The motion detecting unit 203 detects a motion of a human body into which the capsule endoscope 13 is inserted. For example, the motion detecting unit 203 an acceleration sensor that detects acceleration of the human body. The motion detecting unit 203 may be a velocity sensor that detects a velocity of the human body or the like. The human body may be provided with a sensor that can enable wireless communication and detects a motion of the human body, and sensor data wirelessly transmitted from the sensor may be received by the wireless communication unit 200. In this case, the wireless communication unit 200 serves as a motion detecting unit.

The motion analyzing unit 204 analyzes the motion detected by the motion detecting unit 203 and generates motion information on the basis of the analysis result of the motion. The motion information is information for identifying a first case in which the motion of the human body into which the capsule endoscope 13 is inserted is relatively small and a second case in which the motion of the human body is relatively large. When the degree of motion is less than a predetermined threshold value, the motion analyzing unit 204 generates the motion information indicating the first case. When the degree of motion is equal to or greater than the predetermined threshold value, the motion analyzing unit 204 generates the motion information indicating the second case.

The wireless communication unit 200 wirelessly receives an image transmitted from the capsule endoscope 13. The wireless communication unit 200 wirelessly transmits the motion information generated by the motion analyzing unit 204 to the capsule endoscope 13.

In the seventh embodiment, the capsule endoscope 13 controls the mode in consideration of the motion of the human body. Accordingly, it is possible to control the mode more accurately.

(Eighth Embodiment)

In an eighth embodiment of the present invention, the capsule endoscope 11 in the capsule endoscope system 1 shown in FIG. 16 is replaced with the capsule endoscope 14 shown in FIG. 16. The receiver device 20 is replaced with a receiver device 22 shown in FIG. 19.

Figure 19:
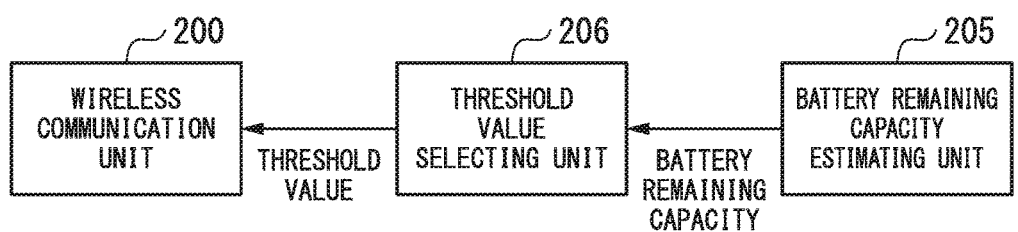
FIG. 19 is a block diagram showing a configuration of a receiver device according to an eighth embodiment of the present invention.

FIG. 19 shows a configuration of the receiver device 22. As shown in FIG. 19, the receiver device 22 includes a wireless communication unit 200 (a second wireless communication unit), a battery remaining capacity estimating unit 205, and a threshold value selecting unit 206.

The battery remaining capacity estimating unit 205 estimates a remaining capacity of a battery of the capsule endoscope 14 using the following method. For example, the battery remaining capacity estimating unit 205 estimates the remaining capacity of the battery of the capsule endoscope 14 on the basis of the number of images captured by the imaging unit 100. The battery remaining capacity estimating unit 205 may estimate the remaining capacity of the battery of the capsule endoscope 14 on the basis of the time elapsing after the motion of the capsule endoscope 14 starts. The battery remaining capacity estimating unit 205 may estimate the remaining capacity of the battery of the capsule endoscope 14 on the basis of a current position (such as a specific organ) of the capsule endoscope 14. For example, the battery remaining capacity estimating unit 205 detects the current position of the capsule endoscope 14 by analyzing the image received from the capsule endoscope 14.

The threshold value selecting unit 206 selects one of a plurality of threshold values depending on the remaining capacity of the battery of the capsule endoscope 14. The threshold values include a threshold value for determination of the mode based on the analysis result of an image and a threshold value for determination of the mode based on the analysis result of data. For example, the threshold value selecting unit 206 includes a table in which the remaining capacity of the battery of the capsule endoscope 14 is correlated with the threshold value. In the table, the remaining capacity of the battery of the capsule endoscope 14 is correlated with the threshold value for determining the mode on the basis of the analysis result of the image and the threshold value for determining the mode on the basis of the analysis result of the data. The smaller the remaining capacity of the battery becomes, the greater the threshold value becomes. That is, the smaller the remaining capacity of the battery, the easier the setting of the first mode in the imaging unit 100 becomes.

The wireless communication unit 200 wirelessly receives an image transmitted from the capsule endoscope 14. The wireless communication unit 200 wirelessly transmits the threshold value selected by the threshold value selecting unit 206 to the capsule endoscope 14. The wireless communication unit 200 may wirelessly transmit information (such as IDs of the threshold values) for designating the threshold value selected by the threshold value selecting unit 206 to the capsule endoscope 14. The wireless communication unit 200 may receive information indicating the remaining capacity of the battery of the capsule endoscope 14 from the capsule endoscope 14. In this case, the wireless communication unit 200 serves as a battery remaining capacity estimating unit.

In the eighth embodiment, when the remaining capacity of the battery of the capsule endoscope 14 is small, the image analyzing unit 102 is set to a smaller threshold value and the data analyzing unit 103 of the capsule endoscope 14. Accordingly, when the mode of the imaging unit 100 is set to the first mode, it is difficult to switch the mode to the second mode. When the mode of the imaging unit 100 is set to the second mode, it is easy to switch the mode to the first mode. Accordingly, it is possible to reduce power consumption of the capsule endoscope 14.

While embodiments of the present invention have been described in detail with reference to the drawings, specific configurations thereof are not limited to the embodiments and include design changes without departing from the gist of the present invention.

The embodiments of the invention have been described above with reference to the drawings, but specific structures of the invention are not limited to the embodiments and may include various modifications without departing from the scope of the invention. The invention is not limited to the above-mentioned embodiments and is limited only by the accompanying claims.

What is claimed is:

1. A capsule endoscope comprising:
   an image sensor configured to image a subject and to acquire an image of the subject, the imaging unit being set to either of a first mode and a second mode; and
   a processor comprising hardware, wherein the processor is configured to:
   acquire data other than the image of the subject; and
   control switching a mode of the image sensor between the first mode and the second mode on the basis of an analysis result of the image of the subject and an analysis result of the data,
   wherein the first mode is activated when a variation of the image of the subject or a variation of the data is less than a predetermined threshold value,
   wherein the second mode is activated when the variation of the image of the subject or the variation of the data is equal to or larger than the predetermined threshold value,
   wherein the processor is configured to control switching the image sensor from the first mode to the second mode according to the analysis result of the data, when the image sensor is currently in the first mode,
   wherein the processor is configured to control switching the image sensor from the second mode to the first mode according to the analysis result of the image of the subject, when the image sensor is in the second mode, and
   wherein the analysis result of the image of the subject corresponds to variation values of a part or all of pixels of the image sensor forming the images of the subject captured at different moments by the image sensor.

2. The capsule endoscope according to claim 1,
   wherein a cycle with which the analysis result of the data is acquired by the processor is shorter than a cycle with which the analysis result of the image is acquired by the processor.

3. The capsule endoscope according to claim 1,
   wherein the processor is configured to acquire at least one of acceleration data, velocity data, angular velocity data, position data, and magnetism data as the data other than the image of the subject.

4. The capsule endoscope according to claim 1,
   wherein an imaging frame rate in the first mode is lower than an imaging frame rate in the second mode.

5. The capsule endoscope according to claim 4,
   wherein the mode of the image sensor is set to any one of the first mode, the second mode, and a third mode,
   wherein an imaging frame rate in the third mode is higher than the imaging frame rate in the second mode, and
   wherein the processor is configured to control switching mode of the image sensor to the first mode or the third mode on the basis of the analysis result of the image when the mode of the image sensor is set to the second mode.

6. The capsule endoscope according to claim 4,
   wherein the mode of the image sensor is set to any one of the first mode, the second mode, and a fourth mode,
   wherein an imaging frame rate in the fourth mode is lower than the imaging frame rate in the first mode, and
   wherein the processor is configured to control switching mode of the image sensor to the first mode on the basis of the analysis result of the data when the mode of the image sensor is set to the fourth mode.

7. The capsule endoscope according to claim 1,
wherein the processor is configured to analyze the image acquired by the image sensor.

8. The capsule endoscope according to claim 1,
wherein the processor is configured to analyze the data acquired by the processor.

9. The capsule endoscope according to claim 1,
wherein a cycle with which the analysis result of the image is acquired by the processor when the mode of the image sensor is set to the second mode is shorter than a cycle with which the analysis result of the image is acquired by the processor when the mode of the image sensor is set to the first mode.

10. The capsule endoscope according to claim 1, further comprising:
a wireless transmitter/receiver configured to receive motion information used for identifying a first case in which motion of a human body is relatively small and a second case in which the motion of the human body is relatively large,
wherein the processor is configured to control switching mode of the image sensor to the second mode on the basis of the analysis result of the data only when the mode of the image sensor is set to the first mode and the motion of the human body is relatively small.

11. The capsule endoscope according to claim 1,
wherein the processor is configured to:
control switching mode of the image sensor to the second mode on the basis of the analysis result of the data regardless of the analysis result of the image when the mode of the image sensor is set to the first mode, and
control switching mode of the image sensor to the first mode on the basis of the analysis result of the image regardless of the analysis result of the data when the second mode is set in the image sensor.

12. The capsule endoscope according to claim 11,
wherein the processor is configured to:
control switching mode of the image sensor to the second mode on the basis of a motion of the capsule endoscope which is the analysis result of the data when the image sensor is set to the first mode, and
control switching mode of the image sensor to the first mode on the basis of the motion of the capsule endoscope which is the analysis result of the image when the image sensor is set to the second mode.

13. The capsule endoscope according to claim 12,
wherein the processor is configured to:
control switching mode of the image sensor to the second mode on the basis of the motion of the capsule endoscope which is calculated from the variation of the data at a plurality of times when the image sensor is set to the first mode, and
control switching mode of the image sensor to the first mode on the basis of the motion of the capsule endoscope which is calculated from the variation of the image at a plurality of times when the image sensor is set to the second mode.

14. The capsule endoscope according to claim 1,
wherein the processor is configured to:
control switching mode of the image sensor to the second mode on the basis of a motion of the capsule endoscope which is the analysis result of the data when the image sensor is set to the first mode, and
control switching mode of the image sensor to the first mode on the basis of the motion of the capsule endoscope which is the analysis result of the image when the image sensor is set to the second mode.

15. The capsule endoscope according to claim 14,
wherein the processor is configured to:
control switching mode of the image sensor to the second mode on the basis of the motion of the capsule endoscope which is calculated from the variation of the data at a plurality of times when the image sensor is set to the first mode, and
control switching mode of the image sensor to the first mode on the basis of the motion of the capsule endoscope which is calculated from the variation of the image at a plurality of times when the image sensor is set to the second mode.

16. A capsule endoscope system comprising
a capsule endoscope and a receiver, wherein
the capsule endoscope includes:
an image sensor configured to image a subject and to acquire an image of the subject in a state in which any one of a first mode and a second mode is set; and
a processor comprising hardware, wherein the processor is configured to acquire data other than the image of the subject and control switching a mode of the image sensor between the first mode and the second mode on the basis of an analysis result of the image of the subject and an analysis result of the data; and
a first wireless transmitter/receiver configured to transmit the image of the subject acquired by the image sensor to the receiver,
wherein the first mode is activated when a variation of the image of the subject or a variation of the data is less than a predetermined threshold value,
wherein the second mode is activated when the variation of the image of the subject or the variation of the data is equal to or larger than the predetermined threshold value,
wherein the processor is configured to control switching the image sensor from the first mode to the second mode according to the analysis result of the data, when the image sensor is currently in the first mode,
wherein the processor is configured to control switching the image sensor from the second mode to the first mode according to the analysis result of the image of the subject, when the image sensor is in the second mode,
wherein the analysis result of the image of the subject corresponds to variation values of a part or all of pixels of the image sensor forming the images of the subject captured at different moments by the image sensor, and
wherein the receiver device includes a second wireless transmitter/receiver configured to receive the image of the subject transmitted from the capsule endoscope.

17. A method of controlling a capsule endoscope, the method comprising:
a first step of acquiring an image of a subject using an image sensor configured to image the subject and to acquire the image of the subject when the image sensor is set to either of a first mode and a second mode;
a second step of acquiring data other than the image of the subject; and
a third step of switching a mode of the image sensor between the first mode and the second mode on the basis of an analysis result of the image of the subject and an analysis result of the data,
wherein the first mode is activated when a variation of the image of the subject or a variation of the data is less than a predetermined threshold value, wherein the second mode is activated when the variation of the image of the subject or the variation of the data is equal to or larger than the predetermined threshold value, wherein during the third step, the mode of the image sensor is switched from the first mode to the second mode according to the analysis result of the data, when the image sensor is currently in the first mode, wherein the processor is configured to control switching the image sensor from the second mode to the first mode according to the analysis result of the image of the subject, when the image sensor is in the second mode, and wherein the analysis result of the image of the subject corresponds to variation values of a part or all of pixels of the image sensor forming the images of the subject captured at different moments by the image sensor.

* * * * *